US012744127B2

(12) United States Patent
Karinka et al.

(10) Patent No.: US 12,744,127 B2
(45) Date of Patent: Sep. 22, 2026

(54) PREDICTING ANALYTE LEVELS BASED ON INTERMITTENT SENSOR DATA

(71) Applicant: ABBOTT DIABETES CARE INC., Alameda, CA (US)

(72) Inventors: Shridhara Alva Karinka, Pleasanton, CA (US); Vivek S. Rao, Alameda, CA (US); Chung-Che Wang, Palo Alto, CA (US); Peter Gary Robinson, Alamo, CA (US); Jennifer Lynn Olson, Alameda, CA (US); Xuandong Hua, Oakland, CA (US); Panganamala Ashwin Kumar, Oakland, CA (US); Sujit R. Jangam, San Mateo, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 0 days.

(21) Appl. No.: 18/787,222

(22) Filed: Jul. 29, 2024

(65) Prior Publication Data

US 2025/0046466 A1 Feb. 6, 2025

Related U.S. Application Data

(60) Provisional application No. 63/530,805, filed on Aug. 4, 2023.

(51) Int. Cl.

| | |
|---|---|
| ***G16H 50/30*** | (2018.01) |
| ***A61B 5/00*** | (2006.01) |
| ***A61B 5/145*** | (2006.01) |

(52) U.S. Cl.

CPC ......... *G16H 50/30* (2018.01); *A61B 5/14532* (2013.01); *A61B 5/6844* (2013.01); *A61B 5/7275* (2013.01); *A61B 5/7475* (2013.01)

(58) Field of Classification Search

CPC ........ G16H 50/30; G16H 50/70; G16H 20/60; G16H 40/63; G16H 40/67; G16H 50/20;

(Continued)

(56) References Cited

U.S. PATENT DOCUMENTS

| | | | |
|---|---|---|---|
| 9,282,922 | B2 | 3/2016 | Haar et al. |
| 10,575,791 | B2 | 3/2020 | Duke et al. |

(Continued)

FOREIGN PATENT DOCUMENTS

| | | | |
|---|---|---|---|
| AU | 2019387464 | A1 | 6/2021 |
| CA | 3121039 | A1 | 6/2020 |

(Continued)

OTHER PUBLICATIONS

Sparacino, Giovanni et al. "Glucose Concentration can be Predicted Ahead in Time From Continuous Glucose Monitoring Sensor Time-Series." IEEE Transactions on Biomedical Engineering, vol. 54, No. 5, May 2007 (Year: 2007).*

(Continued)

*Primary Examiner* — Linh Giang Le

(74) *Attorney, Agent, or Firm* — Workman Nydegger

(57) ABSTRACT

Techniques for predicting analyte levels based on intermittent sensor data are disclosed. First sensor data is acquired from an analyte sensor. The first sensor data reflects analyte levels of a user who is wearing the analyte sensor. The first sensor data is collected over a first time period. Later, a determination is made as to whether data is still being acquired from the analyte sensor. As a result of determining that data is no longer being acquired from the analyte sensor, the first sensor data is classified as intermittent analyte data. The intermittent analyte data is then used to generate predicted analyte level data for the user during a second time (Continued)

period that is subsequent to the first time period. The predicted analyte level data is reflective of the intermittent analyte data.

20 Claims, 20 Drawing Sheets

(58) Field of Classification Search
CPC . A61B 5/14532; A61B 5/6844; A61B 5/7275; A61B 5/7475; A61B 5/0022; A61B 5/681; A61B 5/7264
See application file for complete search history.

(56) References Cited

U.S. PATENT DOCUMENTS

| | | | |
|---|---|---|---|
| 10,664,569 B2 | 5/2020 | Mcmahon et al. | |
| 11,315,674 B2 | 4/2022 | Knapp et al. | |
| 11,367,528 B2 | 6/2022 | Chiu et al. | |
| 11,664,108 B2 | 5/2023 | Dalal et al. | |
| 2020/0176121 A1 | 6/2020 | Dalal et al. | |
| 2020/0196922 A1* | 6/2020 | Kamath | G16H 20/30 |
| 2020/0245913 A1 | 8/2020 | Dalal et al. | |
| 2020/0349448 A1 | 11/2020 | Dalal et al. | |
| 2022/0061710 A1* | 3/2022 | Hadley | A61B 5/7275 |
| 2022/0093234 A1 | 3/2022 | Shima et al. | |
| 2022/0359079 A1 | 11/2022 | Hashemi et al. | |
| 2022/0361778 A1* | 11/2022 | Jepson | A61B 5/7264 |

FOREIGN PATENT DOCUMENTS

| | | | | |
|---|---|---|---|---|
| CN | 113396457 A | 9/2021 | | |
| EP | 3888103 A1 | 10/2021 | | |
| GB | 2596923 B | 12/2022 | | |
| HK | 40053338 | 2/2022 | | |
| IN | 202117028499 | 12/2021 | | |
| JP | 2022-510994 A | 1/2022 | | |
| KR | 10-2021-0099059 A | 8/2021 | | |
| SG | 11202105647 U | 6/2021 | | |
| WO | WO-2016025874 A1 * | 2/2016 | | A61B 5/7275 |
| WO | 2020/113128 A1 | 6/2020 | | |
| WO | 2022/061145 A1 | 3/2022 | | |
| WO | 2022/115709 A2 | 6/2022 | | |
| WO | 2022/235876 A1 | 11/2022 | | |

OTHER PUBLICATIONS

International Search Report and Written Opinion received for PCT Patent Application No. PCT/US2024/040162, mailed on Nov. 18, 2024, 15 pages.

International Preliminary Report on Patentability received for PCT Patent Application No. PCT/US2024/40162, mailed on Feb. 19, 2026, 9 pages.

* cited by examiner

| | A1C Test | Fasting Blood Sugar Test | Glucose Tolerance Test |
|---|---|---|---|
| Diabetes | 6.5% | 126 | 200 |
| Prediabetes | 5.7 – 6.4% | 100-125 | 140-199 |
| Normal | 5.7% or below | 99 or below | 140 or below |

Architecture
900

1800
Acquire First Sensor Data From An Analyte Sensor
1805
Determine Whether Data Is Being Acquired From The Analyte Sensor
1810
Classify The First Sensor Data As Intermittent Analyte Data
1815
Use The Intermittent Analyte Data To Generate Predicted Analyte Level Data For The User During A Second Time Period
1820

PREDICTING ANALYTE LEVELS BASED ON INTERMITTENT SENSOR DATA

CROSS-REFERENCE TO RELATED APPLICATIONS

This application claims the benefit of and priority to U.S. Provisional Patent Application Ser. No. 63/530,805 filed on Aug. 4, 2023 and entitled "PREDICTING ANALYTE LEVELS BASED ON INTERMITTENT SENSOR DATA," which application is expressly incorporated herein by reference in its entirety.

BACKGROUND

A continuous glucose monitor (CGM) is a type of analyte sensing device that tracks a user's blood glucose levels. As used herein, the term "analyte" refers to a substance that is the subject of an analysis. For instance, the CGM tracks glucose levels, and glucose is considered the analyte.

A "glucose level" is also commonly referred to as a "blood sugar" level. The CGM may include a very small sensor that enters or permeates at least partially through the user's skin. Typically, the CGM will acquire a new reading on a periodic basis, such as once every select number of minutes. The CGM includes a wireless transmitter that then sends the reading to a receiving device, such as a smartphone.

The subject matter claimed herein is not limited to embodiments that solve any disadvantages or that operate only in environments such as those described above. Rather, this background is only provided to illustrate one exemplary technology area where some embodiments described herein may be practiced.

BRIEF SUMMARY

In some aspects, the techniques described herein relate to a computer system that predicts analyte levels, the computer system including: a processor system; and a storage system including instructions that are executable by the processor system to cause the computer system to: acquire first sensor data from a first analyte sensor, wherein the first sensor data reflects analyte levels of a user who is wearing the first analyte sensor, and wherein the first sensor data is collected over a first time period; determine whether data is still being acquired from the first analyte sensor; upon a determination that data is no longer being acquired from the first analyte sensor, classify the first sensor data as intermittent analyte data; and use the intermittent analyte data to generate predicted analyte level data for the user during a second time period that is subsequent to the first time period, wherein the predicted analyte level data is reflective of the intermittent analyte data.

In some aspects, the techniques described herein relate to a computer system, wherein the intermittent analyte data is compared against a repository of baseline sensor data for other users.

In some aspects, the techniques described herein relate to a computer system, wherein the predicted analyte level data is compared against metadata associated with the user, wherein the metadata includes one or more of a past glucose level data for the user, location, food consumed, information obtained from a food delivery application, physical activity, or date and time.

In some aspects, the techniques described herein relate to a computer system, wherein the first time period is at least 10 contiguous days.

In some aspects, the techniques described herein relate to a computer system, wherein the first time period is at least 14 contiguous days.

In some aspects, the techniques described herein relate to a computer system, wherein the instructions are further executable to cause the computer system to: acquire new sensor data from a second analyte sensor, different than the first analyte sensor.

In some aspects, the techniques described herein relate to a computer system, the predicted analyte level data is compared against trending data of other users.

In some aspects, the techniques described herein relate to a computer system, wherein the instructions are further executable to cause the computer system to: determine a standard population trend for multiple other users; and compare a profile of the user against the standard population trend.

In some aspects, the techniques described herein relate to a computer system, wherein a profile of the user includes information relating to meals the user has consumed.

In some aspects, the techniques described herein relate to a computer system, wherein a profile of the user tracks glucose levels associated with a same meal that has previously been consumed by the user, and wherein the profile includes a trend of glucose levels for that meal.

In some aspects, the techniques described herein relate to a computer system, wherein a profile of the user includes glucose level trends for different meals the user has consumed, and wherein the profile includes information relating to a comparison between the different meals.

In some aspects, the techniques described herein relate to a computer system, wherein a profile of the user includes glucose trend levels for different users who all consumed a same meal.

In some aspects, the techniques described herein relate to a computer system, wherein a profile of the user includes supplemental information that is relied on to generate the predicted analyte level data.

In some aspects, the techniques described herein relate to a computer system, wherein a profile of the user is compared against profiles of other users who are in a same demographic group.

In some aspects, the techniques described herein relate to a computer system, wherein the instructions are further executable to cause the computer system to: use a profile of the user to determine a behavioral trend for the user; and perform one or more of: recommend a behavior change to the user; or prompt for additional sensor data.

In some aspects, the techniques described herein relate to a method for generating an analyte level profile for a user, the method including: acquiring first sensor data from an analyte sensor, wherein the first sensor data reflects analyte levels of a user who is wearing the analyte sensor, and wherein the first sensor data is collected over a first time period; using the first sensor data to generate a profile for the user, wherein the profile tracks the analyte levels of the user throughout the first time period; during a second time period that is subsequent to the first time period, determining that sensor data is no longer being acquired from the analyte sensor, resulting in the first sensor data being discontinuous analyte data; using the discontinuous analyte data to generate predicted analyte level data for the user; and updating the profile by including the predicted analyte level data.

In some aspects, the techniques described herein relate to a method, wherein the method further includes prompting the user to put either the analyte sensor or a new analyte sensor on to acquire new data.

In some aspects, the techniques described herein relate to a method, wherein the profile includes trend data reflecting how a body of the user is becoming more insulin resistant.

In some aspects, the techniques described herein relate to a method, wherein supplemental data is added to the profile, and wherein the supplemental data includes data from a hemoglobin A1C test.

In some aspects, the techniques described herein relate to a method, wherein the method further includes receiving user input that supplements the discontinuous analyte data, and wherein the user input provides a context for at least some of the discontinuous analyte data.

In some aspects, the techniques described herein relate to a method, wherein the method further includes generating a meal score for a meal the user has consumed.

In some aspects, the techniques described herein relate to a method, wherein the meal score is based on glucose level data collected during a time range after the meal was consumed by the user.

In some aspects, the techniques described herein relate to a method, wherein the meal score is based on one or more of a meal portion size, a meal type, or a listing of ingredients.

In some aspects, the techniques described herein relate to a method, wherein the meal score is based on an uploaded photograph of the meal.

In some aspects, the techniques described herein relate to a method, wherein the profile includes an estimation as to a health level of the meal based on prior meals of a same type as the meal.

In some aspects, the techniques described herein relate to a method, wherein the profile includes an estimation as to a health level of the meal based on how other users having similar profile characteristics as the user responded to the meal.

In some aspects, the techniques described herein relate to a method, wherein the method further includes: identifying a different user who shares similar profile characteristics as the user; determining that the different user is or has previously consumed a meal similar to a meal the user is or will consume; and use meal-specific analyte levels of the different user to predict meal-specific analyte levels for the user for said meal.

In some aspects, the techniques described herein relate to a method, wherein the profile includes glucose fingerprints for the user for different meals.

In some aspects, the techniques described herein relate to a method, wherein a machine learning algorithm, which is trained based on analyte training data, generates the predicted analyte level data.

In some aspects, the techniques described herein relate to a method, wherein the method further includes training a machine learning algorithm based on the discontinuous analyte data.

In some aspects, the techniques described herein relate to a method for generating a health model for a user the method including: acquiring first sensor data from an analyte sensor, wherein the first sensor data reflects a physiological response of a user who is wearing the analyte sensor, and wherein the first sensor data is collected over a first time period; using the first sensor data to generate the health model for the user, wherein the health model tracks the physiological response of the user throughout the first time period; during a second time period that is subsequent to the first time period, determining that updated sensor data is no longer being acquired from the analyte sensor, resulting in the first sensor data being periodic sensor data; using the periodic sensor data to generate predicted physiological response data for the user during the second time period; and updating the model by including the predicted physiological response data.

In some aspects, the techniques described herein relate to a method, wherein the method further includes: facilitating peer to peer sharing of sensor data; and identifying users who share physiological response characteristics that are similar to the user.

In some aspects, the techniques described herein relate to a method, wherein the method further includes: accessing one of a calendar or a global positioning system (GPS) data to acquire supplemental data about the user; and associating supplemental data with periodic sensor data using time information, wherein the supplemental data provides context for at least a portion of the periodic sensor data.

In some aspects, the techniques described herein relate to a method, wherein the method further includes providing a coaching prompt to the user during the second time period.

In some aspects, the techniques described herein relate to a method, wherein the method further includes: determining that the predicted physiological response data is stale; and submitting a recommendation to the user to facilitate one or more of: acquiring new sensor data or prompting the user to use a different analyte sensor.

In some aspects, the techniques described herein relate to a method, wherein the predicted physiological response data is determined to be stale after a determined time period has elapsed with no new data from the analyte sensor.

In some aspects, the techniques described herein relate to a method, wherein the first time period is one week or greater.

In some aspects, the techniques described herein relate to a method, wherein the first time period is about one month.

In some aspects, the techniques described herein relate to a method, wherein the first time period is between about one month and about six months.

In some aspects, the techniques described herein relate to a method, wherein the method further includes: receiving supplemental fitness data; and using the supplemental fitness data to update the health model.

In some aspects, the techniques described herein relate to a method, wherein the supplemental fitness data is one of: blood pressure data, step tracker data, or heart rate data.

In some aspects, the techniques described herein relate to a device, wherein the frequency is based on one or more characteristics of the user.

In some aspects, the techniques described herein relate to a method, wherein the method is implemented by a service, and wherein the service is a cloud service.

In some aspects, the techniques described herein relate to a method, wherein supplemental data is also used to generate the health model, and wherein different weights are applied to the periodic sensor data and the supplemental data.

In some aspects, the techniques described herein relate to a method, wherein the periodic sensor data includes glucose level data, and wherein the glucose level data is provided a highest weight as compared to weights provided to the supplemental data.

In some aspects, the techniques described herein relate to a method, wherein population matching is performed to identify one or more other users who share similar characteristics as the user.

In some aspects, the techniques described herein relate to a method, wherein the similar characteristics include one or more of age, sex, location, activity level, or occupation.

In some aspects, the techniques described herein relate to a method, wherein a confidence level is determined, and wherein the confidence level reflects how closely the user is similar to the one or more other users.

In some aspects, the techniques described herein relate to a method, wherein the one or more other users are family members or coworkers.

In some aspects, the techniques described herein relate to a method, wherein supplemental data is also fed as input to the health model, and wherein the supplemental data is obtained from one or more of a glucose ketone sensor, a glucose ketone alcohol sensor, or a glucose ketone alcohol lactate sensor.

In some aspects, a computer system implements a service that generates a glucose level profile for a user, where the glucose level profile is based on intermittent baseline glucose data received from a continuous glucose monitoring (CGM) sensor and where the glucose level profile includes predicted glucose data that is predicted from the intermittent baseline glucose data, said computer system comprising: a processor system; and a storage system comprising instructions that are executable by the processor system to cause the computer system to service to: acquire first sensor data from a first CGM sensor, wherein the first sensor data reflects glucose levels of a user who is wearing the first CGM sensor, and wherein the first sensor data is collected over a first time period; use the first sensor data to generate a profile for the user, wherein the profile tracks the glucose levels of the user throughout the first time period; during a second time period that is subsequent to the first time period, determine that updated sensor data is either (i) no longer being acquired from the first CGM sensor or (ii) below a threshold level of accuracy, resulting in a determination that the first sensor data is to be classified as being intermittent glucose data; in response to said determination, use the intermittent glucose data to generate predicted glucose level data for the user, wherein the predicted glucose level data is reflective of predicted glucose levels for the user during the second time period; update the profile by including the predicted glucose level data; during a third time period that is subsequent to the second time period, acquire second sensor data from a second CGM sensor worn by the user; and update the profile by including the second sensor data.

In some aspects, the profile is updated via a machine learning engine.

In some aspects, the service is implemented either on a local client device or in a cloud environment.

In some aspects, the second CGM sensor is different than the first CGM sensor.

In some aspects, the second CGM sensor is the same as the first CGM sensor.

In some aspects, a machine learning engine analyzes the second sensor data.

In some aspects, a machine learning engine includes analytics on the first sensor data, the predicted glucose level data, and/or the second sensor data in the profile.

In some aspects, a machine learning engine, which updates the profile, is included as a part of the service.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages will be set forth in the description which follows, and in part will be obvious from the description, or may be learned by the practice of the teachings herein. Features and advantages of the invention may be realized and obtained by means of the instruments and combinations particularly pointed out in the appended claims. Features of the present invention will become more fully apparent from the following description and appended claims, or may be learned by the practice of the invention as set forth hereinafter.

BRIEF DESCRIPTION OF THE DRAWINGS

In order to describe the manner in which the above-recited and other advantages and features can be obtained, a more particular description of the subject matter briefly described above will be rendered by reference to specific embodiments which are illustrated in the appended drawings. Understanding that these drawings depict only typical embodiments and are not therefore to be considered to be limiting in scope, embodiments will be described and explained with additional specificity and detail through the use of the accompanying drawings in which.

DETAILED DESCRIPTION

Figure 1:
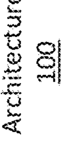
FIG. 1 illustrates an example architecture in which sensor data is being acquired and analyzed.
Figure 1:
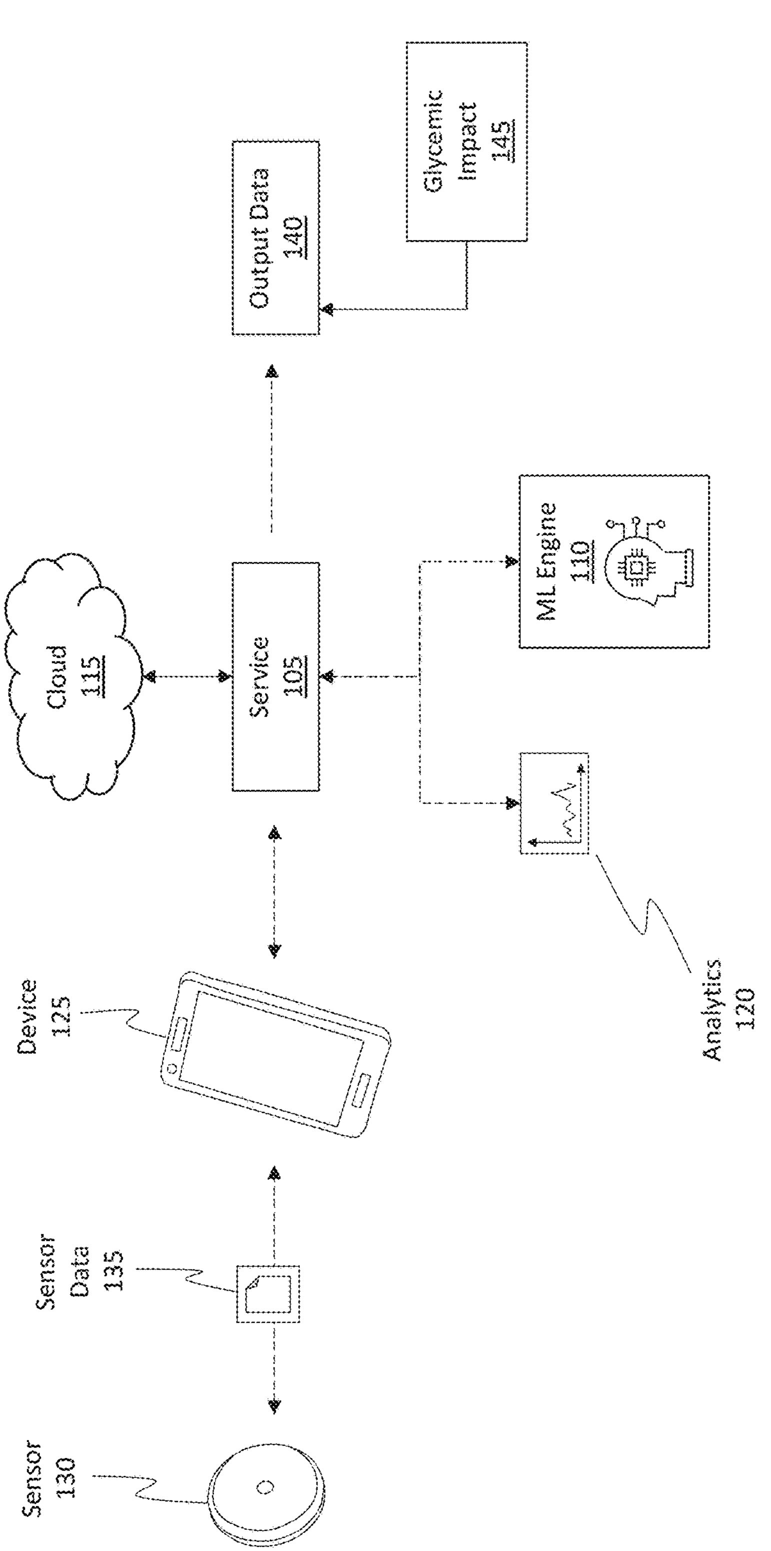

"Pre-diabetes" refers to a health condition where a person's blood sugar levels are typically higher than a normally accepted threshold level yet are lower than what a diabetic person's levels are. Interestingly, of those individuals who actually have pre-diabetes, a vast majority of those pre-diabetics (e.g., some estimates say as high as 80%) do not know they actually have pre-diabetes.

One of the primary reasons as to why individuals are not aware if they have pre-diabetes is because people who are not diagnosed with diabetes typically are not encouraged to track their blood sugar levels. As a result, many people go through prolonged time periods in which they do not know or are not aware of their blood sugar levels. Diabetics are often encouraged to track blood sugar level by periodically pricking a finger (traditional blood glucose monitoring) or wearing a continuous glucose monitor (CGM).Non-diabetic and pre-diabetic individuals may not know what a CGM is or how to use it. Traditionally, therefore, it is the case that pre-diabetic individuals do not monitor their glucose levels outside of a doctor's office.

A further complication for pre-diabetics in tracking blood sugar levels relates to reading the CGM data. Traditionally, a dedicated CGM reader or an application on a phone required continuous or near continuous data from the CGM sensor in order to operate properly. For instance, while the user is wearing the CGM, the application tracks and analyzes the data. When the user stops wearing the CGM, the application effectively ceases to operate because it relies almost exclusively on the sensor data. Because the application's features rely on the sensor data, if no sensor data is available, then the application essentially stops operating (e.g., stops outputting insights regarding actual or predicted glucose levels). When people without diabetes or with pre-diabetes use CGMs, these individuals may only wear the CGM periodically or intermittently. Thus, the application provides worthwhile insights only while the pre-diabetic is wearing the CGM, but the times when the pre-diabetic is not wearing the CGM, the application does not give the user insight into their glucose levels or response to lifestyle factors like diet and activity.

The disclosed embodiments provide various improvements, benefits, and practical applications to the technical field of sensor data collection and analysis. In particular, the embodiments are beneficially able to operate even when intermittent (aka "sparse" or "periodic" or "baseline") sensor data is available. The embodiments use this intermittent data to generate predicted data, which uses whatever sensor data is available as an initial baseline so as to generate predicted data that is usable during instances in which actual or current sensor data is not available. This predicted data is then made available to an application. The application can then provide various insights to a user, even when sensor data is not actively being acquired. As a result, the application can be continued to be used even when an analyte sensor (e.g., the CGM) is not being worn by a user.

The disclosed embodiments beneficially enable users to better manage their lifestyles via the use of an improved application for analyte data and via the generation of predicted analyte or sensor data. What this means is that the embodiments provide various mechanisms to enable all types of users, including pre-diabetics, to better manage their own lifestyles. As a result, significant advantages and value-adding experiences are provided to individuals who may only periodically use a sensor.

Additionally, the disclosed embodiments provide an improved user experience with respect to an analyte sensor and with respect to an application that uses data obtained from the analyte sensor. The embodiments also enable the collected sensor data and even the predicted data to be shared with other individuals and/or health professionals. Furthermore, the disclosed application can operate using the predicted data to generate various different recommendations, scores, or even alerts. The disclosed embodiments also enable data to be analyzed to detect trends. Such trends can operate as a basis for which a recommendation is generated, such as a recommendation to visit a health care specialist.

Throughout this disclosure, there are many references to glucose levels and CGMs. A person skilled in the art, however, will appreciate how the disclosed principles can be applied to any type of analyte and to any type of analyte sensor, including both invasive sensors (i.e. a sensor that at least partially enters a patient's body) and non-invasive sensors (i.e. a sensor that does not enter the patient's body). Examples of analytes include, but are not limited to, glucose, ketone, lactate, alcohol, and others. Therefore, even though a majority of the examples are with respect to glucose levels and CGMs, the principles should be viewed as being more broadly applicable.

Example Architectures

FIG. 1 illustrates an example architecture 100 that can be used to achieve the benefits mentioned above. Architecture 100 is shown as including a service 105. As used herein, the term "service" refers to an automated program that is tasked with performing different actions based on input. In some cases, service 105 can be a deterministic service that operates fully given a set of inputs and without a randomization factor. In other cases, service 105 can be or can include an artificial intelligence (AI) or machine learning (ML) engine, as shown by ML engine 110. With the ML engine 110, service 105 can operate even when faced with various different randomization factors.

As used herein, reference to any type of ML or AI may include any type of ML algorithm or device, convolutional neural network(s), multilayer neural network(s), recursive neural network(s), deep neural network(s), decision tree model(s) (e.g., decision trees, random forests, and gradient boosted trees) linear regression model(s), logistic regression model(s), support vector machine(s) ("SVM"), AI device(s), or any other type of intelligent computing system. Any amount of training data may be used (and perhaps later refined) to train the ML algorithm to dynamically perform the disclosed operations.

In some implementations, service 105 is a cloud service operating in a cloud environment, such as cloud 115. In some implementations, service 105 is a local service operating on a local device (e.g., sensor 130, device 125, and/or any other device). In some implementations, service 105 is a hybrid service that includes a cloud component operating in the cloud 115 and a local component operating on a local client device. These two components can communicate with one another.

Service 105 is tasked with various operations that include collecting sensor data, analyzing that sensor data, and determining the impact of that sensor data with respect to a user associated with the sensor data. To do so, service 105 can include an analytics 120 component that is capable of performing data analysis on the collected sensor data. In some examples, analytics 120 and ML Engine 110 can be the same component.

As shown in FIG. 1, service 105 can communicate with a device 125. Device 125 can be any type of personal device, including any type of wearable device or mobile device. Examples of device 125 include, but certainly are not limited to, any type of device reader, smart phone, tablet, laptop, desktop, wearable device, and so on. Device 125 is shown as communicating with a sensor 130 and is further shown as receiving sensor data 135 from the sensor 130. Sensor 130 is the component that collects the sensor data 135. In some cases, device 125 and sensor 130 can be implemented on the same device.

Sensor 130 can be any type of sensor. One particular example of sensor 130 includes a CGM. A CGM operates by inserting a small sensing unit under a person's skin. This sensing unit then measures that person's interstitial glucose levels. Typically, this sensing unit acquires new data at a periodic rate, such as once every selected number of minutes, although the data could also be collected continuously. That data is represented as sensor data 135 in FIG. 1.

Device 125 communicates with sensor 130 using any type of near-field wireless communication technology, such as BLUETOOTH. As a result, sensor data 135 is transmitted from sensor 130 to device 125 over that communication protocol. Service 105 can communicate with device 125 via any type of wireless communication protocol as well. In some implementations, the communication protocol is a BLUETOOTH protocol. In some implementations, the protocol is a wireless fidelity (Wi-Fi), near field communication (NFC), and/or Internet Protocol (IP). Often, device 125 transmits the sensor data 135 to the cloud 115, where that sensor data 135 is then stored in a repository that is accessible to service 105.

In some implementations, the sensor data 135 is encrypted or otherwise integrity protected to ensure tampering does not occur. Also, in some implementations, any personally identifiable information (PII) is stripped from sensor data 135 prior to it being stored in the cloud 115.

Figure 2:
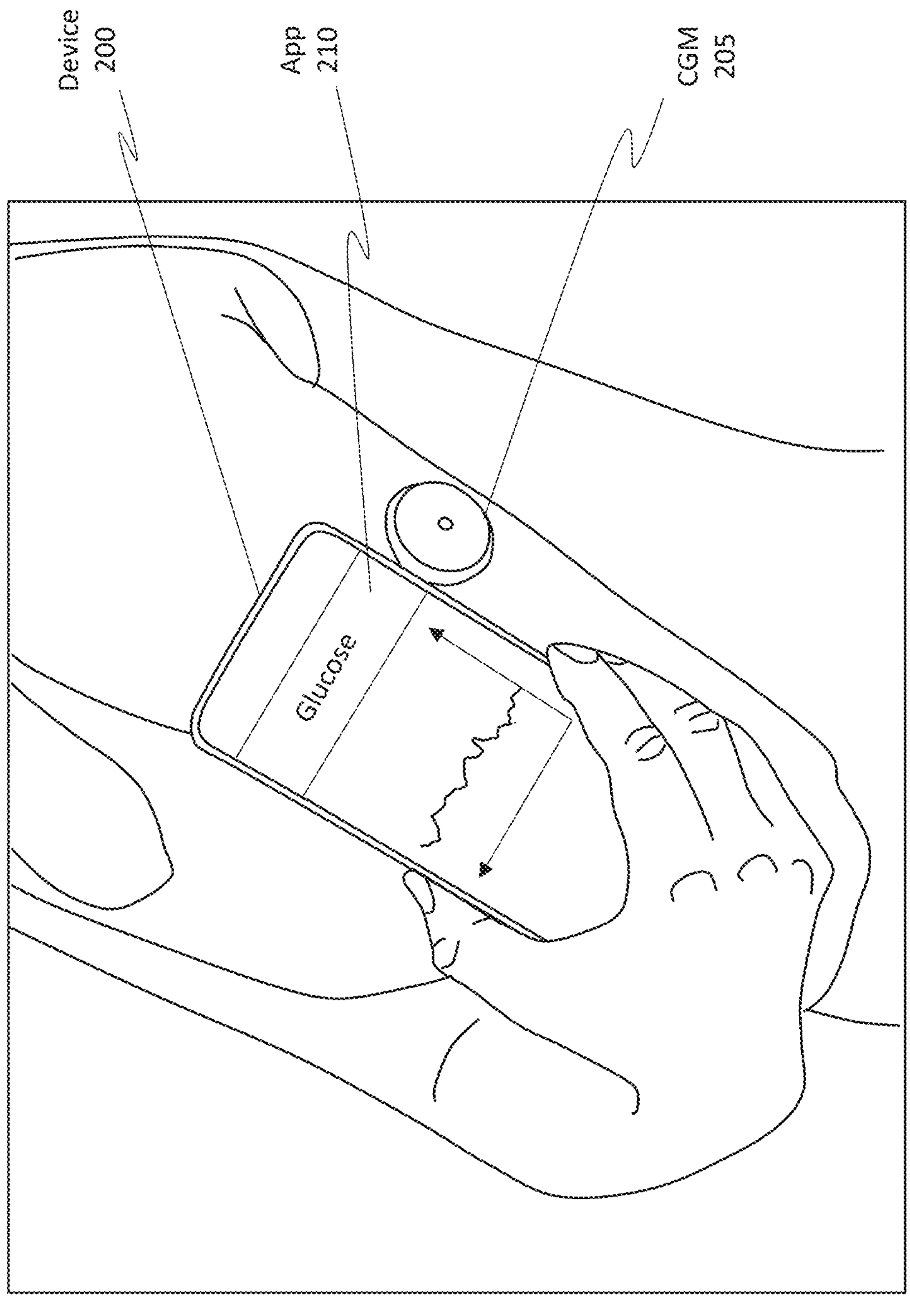
FIG. 2 illustrates an example of an analyte sensor in the form of a continuous glucose monitor.

Service 105 then uses its analytics 120 component and/or the ML engine 110 to analyze the sensor data 135. Service 105 generates output data 140 as a result of performing that analysis. In the scenario where sensor 130 is a CGM and where the sensor data 135 reflects glucose levels for a user, the output data 140 can reflect glycemic insights such as a glycemic impact 145 for the user. Glycemic impact 145 generally refers to a patient's bodily state with respect to blood sugar levels. FIG. 2 provides another example.

FIG. 2 shows a device 200, which is representative of device 125 from FIG. 1. Device 200 is in communication with a CGM 205, which is representative of sensor 130. CGM 205 is currently affixed to the user's arm and is tracking the user's glucose levels. Device 200 is hosting an application (or simply "app") 210. App 210 provides a visualization of the tracked data (e.g., a graph or trace of glucose levels over a period of time).

Figure 3:
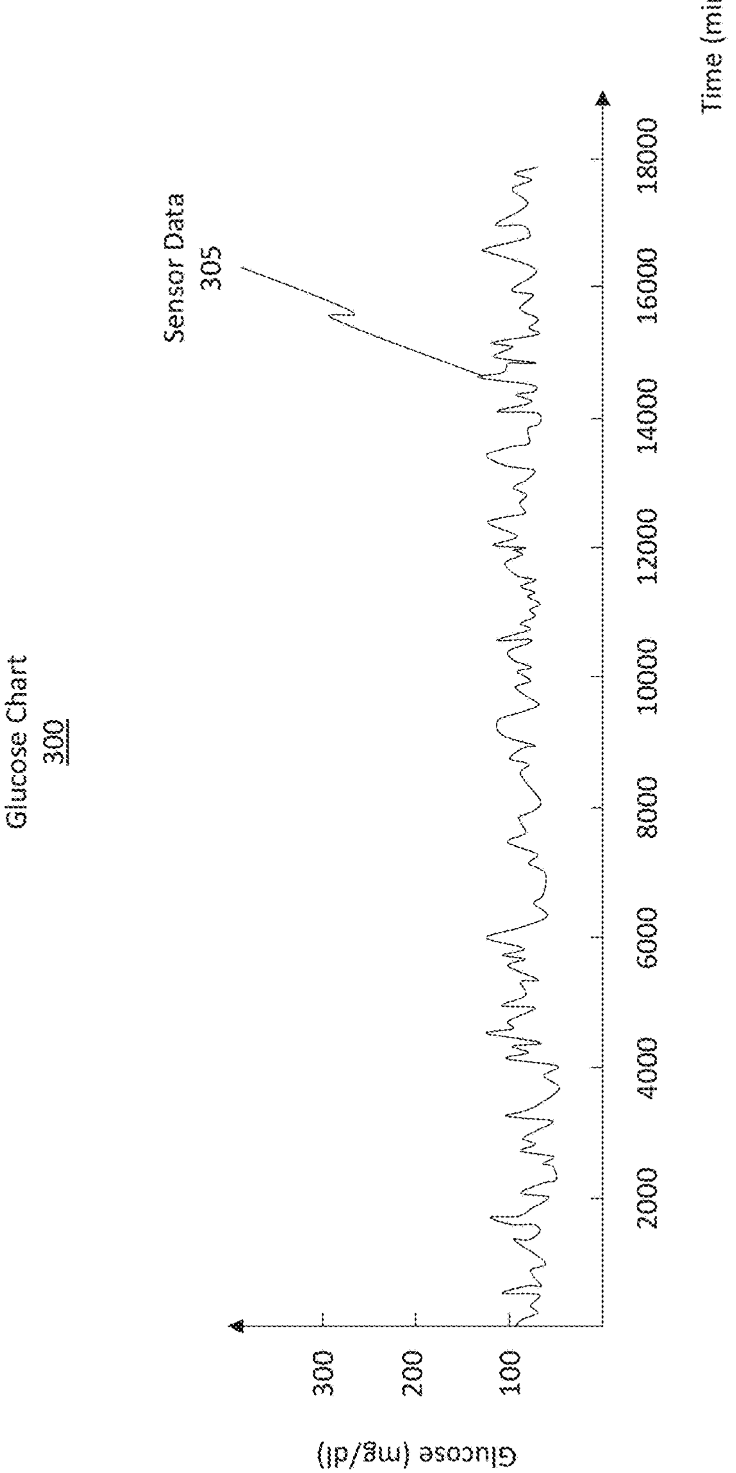
FIG. 3 illustrates a chart that is plotting data obtained from the analyte sensor.

FIG. 3 shows a glucose chart 300, which can be displayed by the app 210 of FIG. 2. Glucose chart 300 is displaying the sensor data 305, which is reflective of the user's glucose levels over a period of time. For instance, the horizontal axis reflects the glucose levels over a minutes-based time period.

Figure 4:
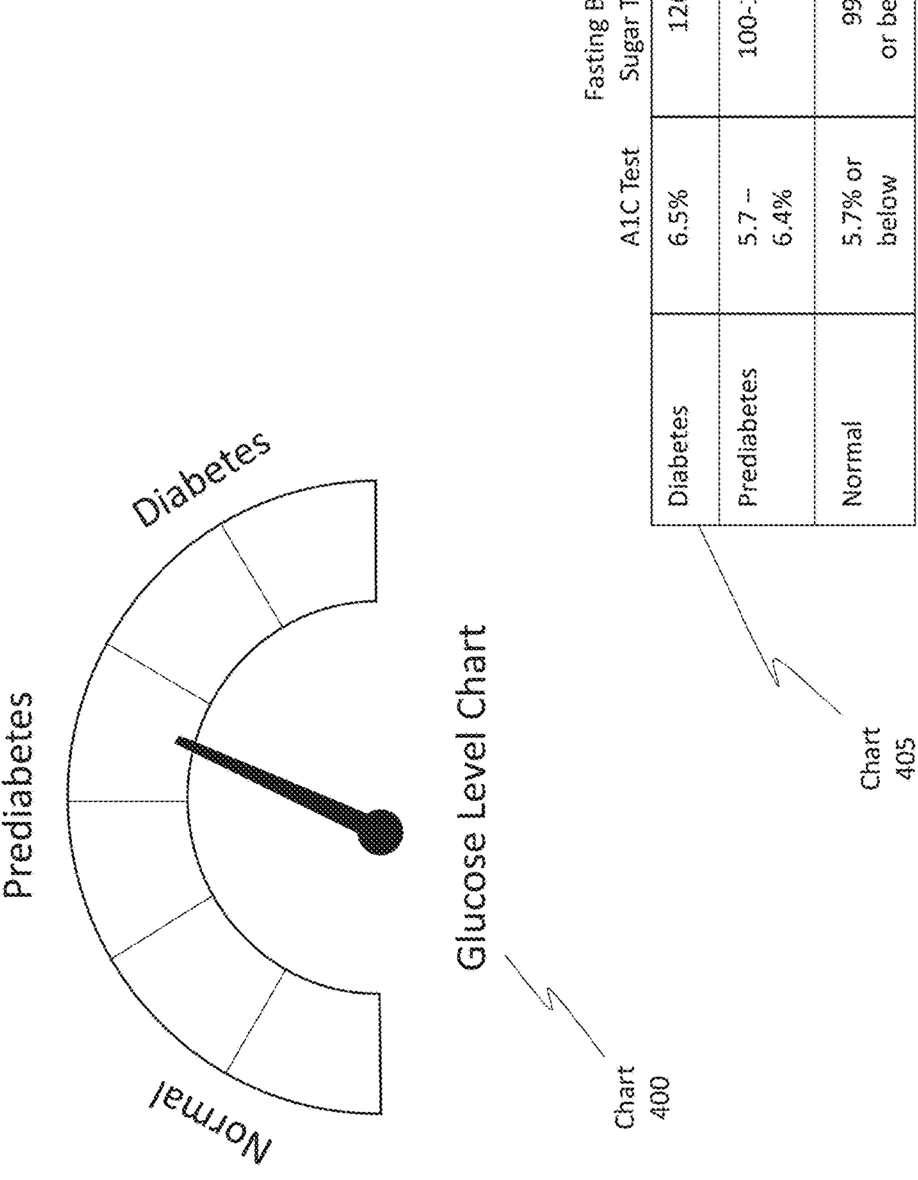
FIG. 4 illustrates various other charts related to the analyte sensor data.

FIG. 4 shows some additional information that can be provided by the app 210 of FIG. 2. In particular, FIG. 4 shows a first chart 400 and a second chart 405. Chart 400 is updated to reflect whether the user has glucose levels corresponding to a normal range, a pre-diabetic range, or a diabetic range. Chart 400 is thus updated based on the specific user's glucose levels, as determined by the user's CGM.

Chart 405 shows standard data or measurement thresholds that determine whether the user's glucose levels are normal, pre-diabetic, or diabetic. For instance, if the user's fasting glucose levels are 99 or below, then the user's levels are considered normal. If the user's fasting glucose levels are between 100 and 125, then the user's levels are considered pre-diabetic. To complete the example, if the user's fasting glucose levels are 126 or higher, then the user's glucose levels are considered to be diabetic. Thus, chart 405 provides various benchmarks against which the user can compare his/her glucose levels.

For users whose glucose levels are in the normal range, those users typically do not need to monitor their glucose levels often. There are many tools and protocols available to make sure that these types of individuals continue to live a healthy lifestyle. On the other hand, for users whose glucose levels are in the diabetic range, those users should monitor their glucose levels frequently. Diabetics often collect glucose level data multiple times a day, if not continuously or nearly continuously, via their CGMs. There are many sensing tools and protocols available for diabetics to make sure that they live a healthy lifestyle. For instance, app 210 from FIG. 2 is often configured specifically for diabetics.

Figure 5:
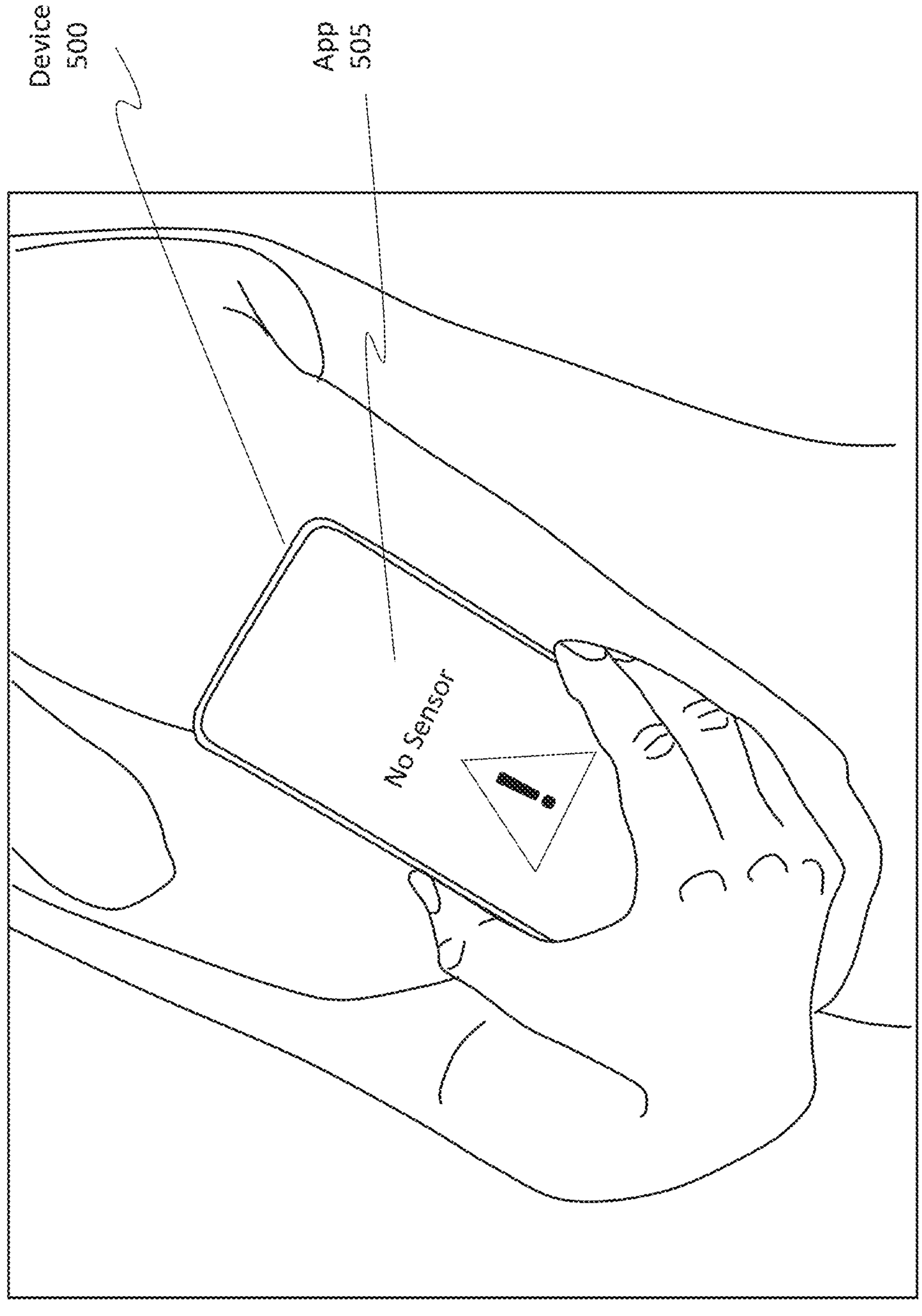
FIG. 5 illustrates an example scenario where analyte sensor data is not being acquired.
Figure 6:
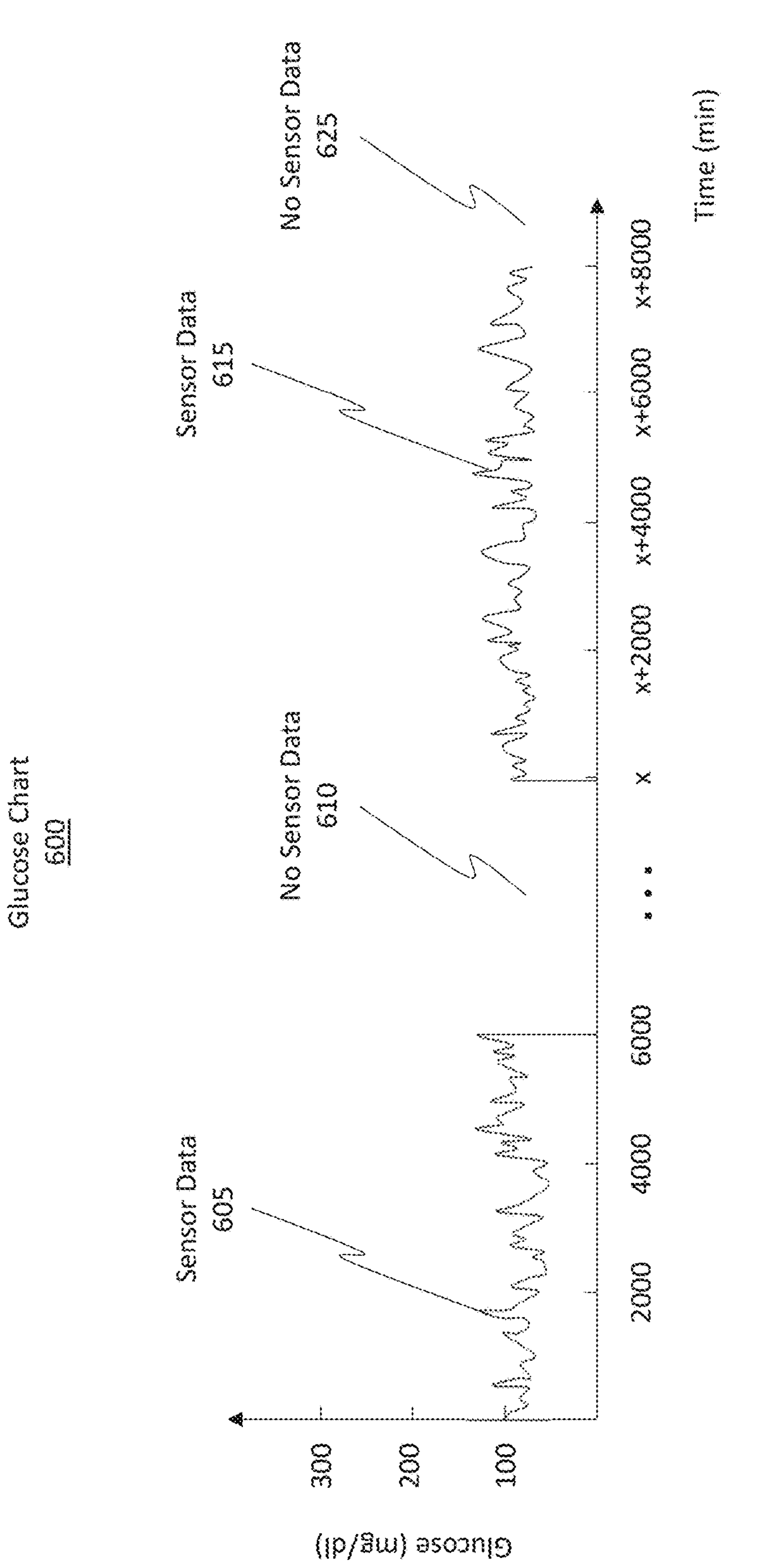
FIG. 6 illustrates a chart showing how data is intermittently or sparsely being obtained from one or more analyte sensors.

Pre-diabetics, on the other hand, are often not provided tools or protocols to help them live the type of lifestyle they should in order to be healthy. For instance, pre-diabetics are often not advised to wear a CGM continuously so as to monitor their glucose levels. Similarly, pre-diabetics are often not advised, or perhaps not adequately advised, on what foods to eat, when to eat that food, or what portions of food to eat. As another example, app 210 from FIG. 2 is often configured in a manner that is inadequate for pre-diabetics and thus often fails to satisfy the desires of pre-diabetics. This failure often occurs because pre-diabetic individuals often do not continuously wear a CGM. As a result, app 210 is provided only with sparse data and often cannot perform a satisfactory analysis using that sparse data. FIGS. 5 and 6 are illustrative.

FIG. 5 shows an example scenario involving a device 500 and an app 505, which are representative of the device 200 and app 210 of FIG. 2, respectively. Notice, in this example scenario, the user is not currently wearing an active CGM sensor. As a result, device 500 is not able to obtain updated sensor data and does not display glucose information.

FIG. 6 shows a glucose chart 600 that includes first sensor data 605 obtained during a first time period a first CGM sensor. At time 6,000, the user stopped wearing the first CGM sensor, or the CGM stopped obtaining data for some reason (e.g., the sensor expired, fell off, was damaged). Thus, there is a period of time 610 during which no sensor data is obtained. During this time period, the usefulness of app 210 from FIG. 2 is significantly reduced, or ceases all together, because the functions of app 210 rely on up-to-date sensor data.

Later, second sensor data 615 is again obtained (e.g., using the first CGM sensor or a second CGM sensor, different than the first sensor). For instance, the user may have obtained a new sensor that now works, or the user reaffixed the sensor to his/her arm. FIG. 6 thus shows a scenario in which intermittent data 620 (e.g., sensor data 605 and 615) (aka sparse data or periodic data) is obtained. Later, there is another period of time 625 in which no sensor data is obtained. Traditionally, applications and analytics engines were not able to sufficiently analyze intermittent data 620 in a manner that would provide worthwhile output to a user during periods in which sensor data was not being collected (e.g., time periods 610 and 625).

The disclosed embodiments, on the other hand, are able to operate using intermittent data. Accordingly, attention will now be directed to FIG. 7, which illustrates an improved architecture 700 that includes a service 705. Service 705 is configured to generate a glucose level profile for a user, where the glucose level profile is based on intermittent baseline glucose data received from a CGM sensor (e.g., sensor data 605 and 615) and where the glucose level profile includes predicted glucose data that is predicted from the intermittent baseline glucose data. Optionally, the profile can be or can include a model, including any type of ML model. For example, service 705 could be used to predict glucose data during period 625 of FIG. 6 using sensor data 605 and/or 615.

Service 705 can operate in the cloud 710 or can communicate with the cloud 710. Service 705 includes an analytics

715 component and/or an ML engine 720. Service 705 can also communicate with a device 725 that is hosting an application.

In this example scenario, sensor 730 (e.g., a CGM sensor) is now decoupled (e.g., as shown by decouple 735) from communicating with the device 725 for some period of time, resulting in the scenario where intermittent sensor data is generated. Being "decoupled" includes various scenarios, including one where no sensor is present and one where a sensor may be present, but it is not providing data, or the quality of that data is below a threshold level of accuracy or quality.

Architecture 700 shows a scenario where an initial set of baseline data 740 is generated by the sensor 730 and is provided to the device 725. As an example, first sensor data 605 and/or 615 from FIG. 6 can be representative of the baseline data 740. Baseline data generally refers to an initial or intermittent collection of data that can be subsequently used to perform various different actions. Typically, a threshold amount of data is needed to qualify as a baseline set of data. Notably, however, that threshold is dynamic and can be set to any value. For instance, the threshold amount of data may be a select number of minutes worth of data, a select number of hours worth of data, or perhaps a select number of days worth of data. The collected data may be contiguous (e.g., sensor data 605) or sparse (e.g., sensor data 605 and sensor data 615). As will be described in more detail below, the embodiments are able to generate predicted data based on this baseline data. The point at which the predicted data becomes stale (i.e., the accuracy or quality of the data falls below a threshold level) can be dependent on the amount of data included in the baseline data and/or duration of time from which the baseline data was obtained. For instance, a larger amount of baseline data may prolong the validity of predicted data before it becomes stale because more trends can be learned from the larger amount of data. A lesser amount of baseline data may result in the predicted data becoming stale faster because fewer trends can be learned from the data. In some examples, baseline data may become stale after a threshold period of time (e.g., 2 weeks, 4 weeks, 3 months, or any other period of time) after it was obtained.

At some point, sensor 730 is no longer acquiring, or no longer transmitting, updated sensor data. As a result, service 705 is presented with a scenario where intermittent data is available as opposed to continuous up-to-date data. When up-to-date data is again available, service 705 can rely on that data to generate results.

In accordance with the disclosed principles, service 705 is also configured to acquire supplemental data 745 from one or more sources external or independent relative to sensor 730. Supplemental data 745 can include any type of additional information.

Some non-limiting examples of supplemental data 745 include meal data (e.g., carbohydrate content, portions) entered by the user or collected from an app (e.g., meal tracking app, restaurant app, meal delivery app), data from a hemoglobin A1C test, user input that supplements the baseline sensor data (e.g., the user input may provide a context for at least some of the baseline sensor data), calendar data or global positioning system (GPS) data about the user to thereby provide context for the baseline sensor data, supplemental fitness data (e.g., blood pressure data, step tracker data, heart rate data, exercise type, exercise duration, exercise intensity), supplemental data obtained from one or more of a glucose ketone sensor, a glucose ketone alcohol sensor, or a glucose ketone alcohol lactate sensor. Any other type of supplemental data can also be provided to service 705.

As a result, the embodiments are able to receive supplemental data, including supplemental fitness data. As will be discussed shortly, this supplemental fitness data may then be used to update a health model, profile, or other repository of information. Optionally, the supplemental fitness data may be one of: blood pressure data, step tracker data, or heart rate data.

Figure 8:
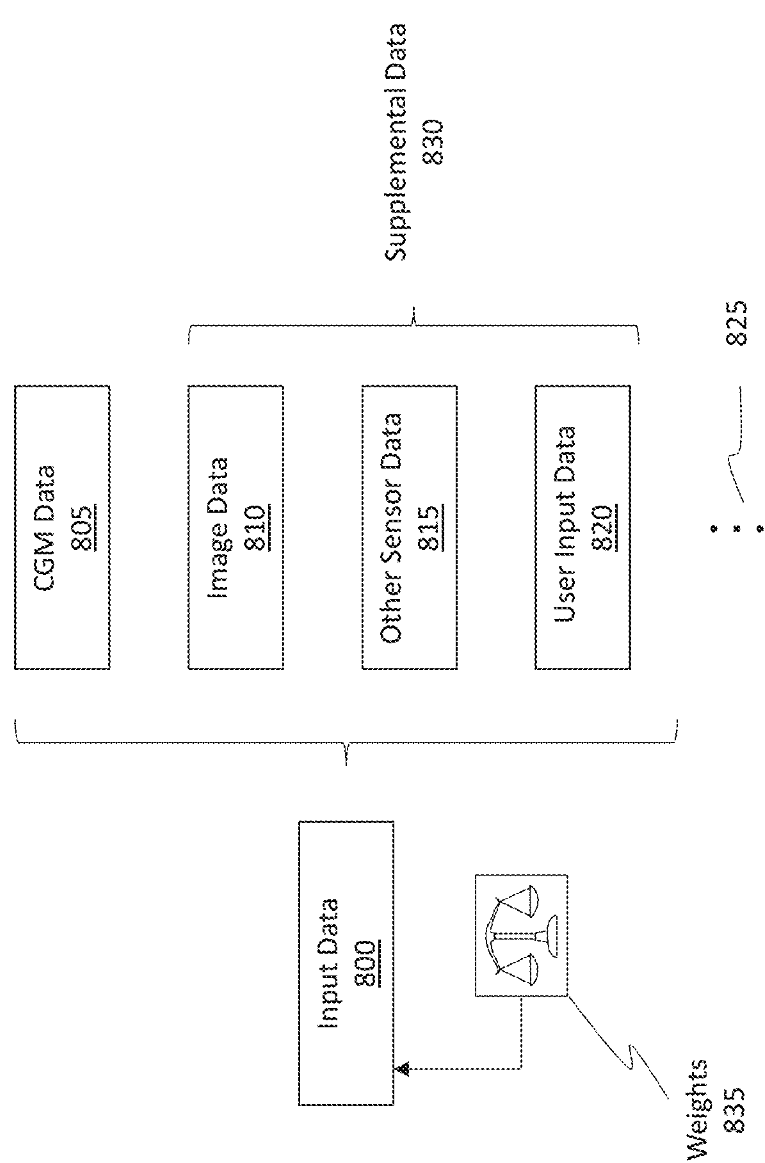
FIG. 8 illustrates various different types of input data.
Figure 8:
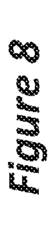

Service 705 receives the baseline data 740 as well as any other intermittent data (e.g., perhaps historical data collected at an earlier time period or perhaps other data obtained from other devices) and supplemental data 745. That is, such data is provided as input to service 705. Turning briefly to FIG. 8, FIG. 8 provides some additional details on this input.

Figure 7:
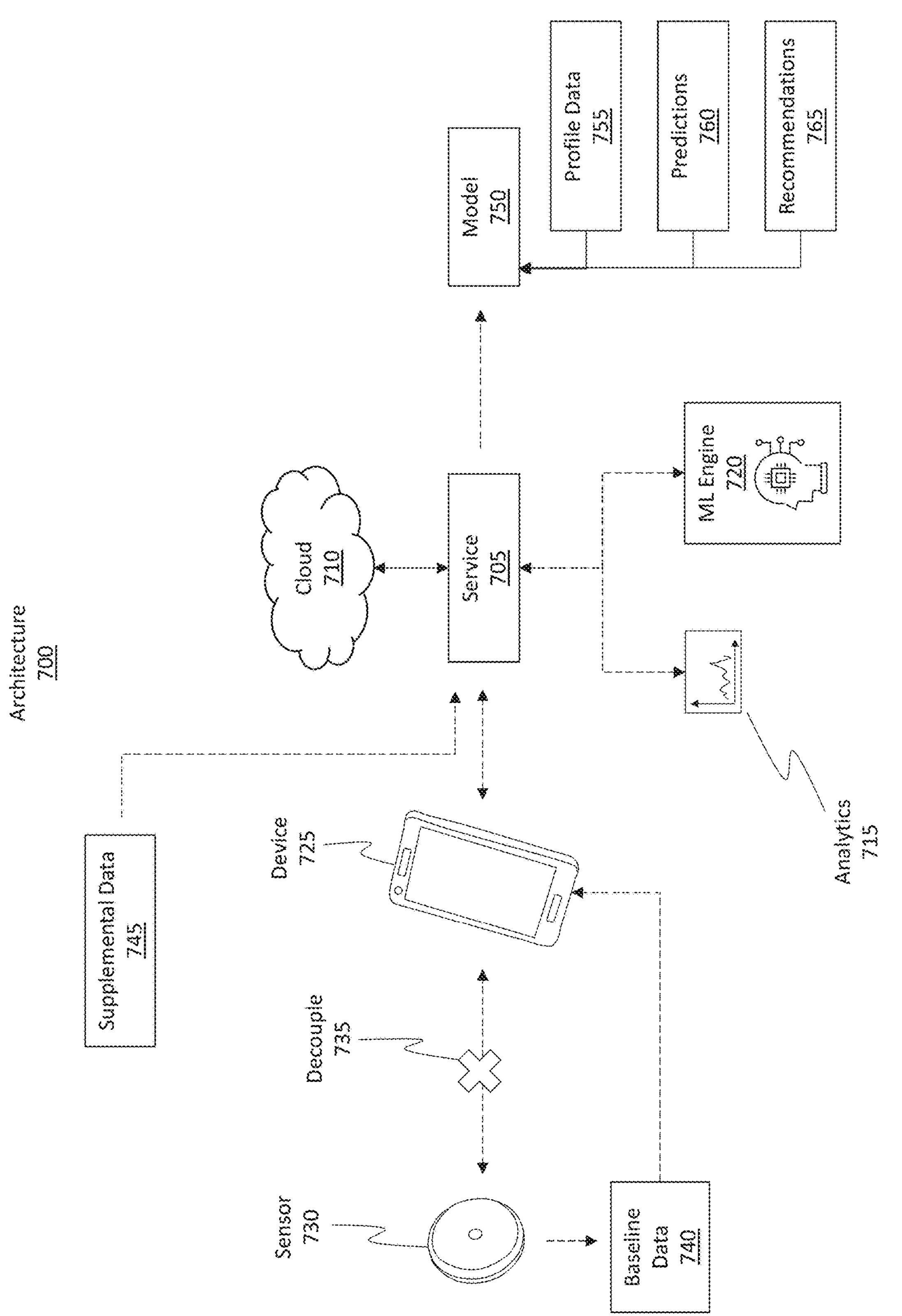
FIG. 7 illustrates another example architecture that operates using intermittent data.

FIG. 8 shows input data 800 that is provided to service 705 from FIG. 7. Input data 800 includes CGM data 805, image data 810, other sensor data 815, and user input data 820. The ellipses 825 demonstrates how other data can be provided to service 705 as well, such as manual input or connecting data communications with other devices or applications. The image data 810, other sensor data 815, and the user input data 820 are examples of supplemental data 830, which is representative of supplemental data 745 from FIG. 7.

FIG. 8 also shows different weights 835. Different weights 835 can be applied to the different types of input data 800. For instance, the actual sensor or analyte data (e.g., CGM data 805) may be provided a highest weight while the supplemental data 830 may be provided lower weights. In some implementations, different weights can be used for different time periods and/or different conditions (e.g., bodily conditions of a patient or perhaps even environmental conditions). Weights for supplemental data can optionally change depending on the availability of CGM data. Similarly, weights for current CGM data may be highest whereas weights for baseline data may change over time until eventually that baseline data is determined to be stale. These weights can be used to later generate a score for the user, where that score can then be included in the user's health model or profile. This score provides the user with a quick snapshot or overview of the user's health.

As mentioned, in some scenarios, the supplemental data can be used to generate a health model or profile. Optionally, different weights may be applied to the sensor data (e.g., the intermittent, sparse, or periodic sensor data) and the supplemental data. For instance, supposing the periodic sensor data includes glucose level data, the glucose level data may be provided a highest weight as compared to weights provided to the supplemental data.

Regarding the image data 810, service 705 is able to receive images of a user's food choices and other activities. Service 705 includes logic to analyze image content to determine what type of food a user is consuming and/or what type of activity a user is involved in. This logic enables service 705 to predict or estimate the nutritional value and ingredient list for the food and/or estimate the health aspects of a given activity.

Optionally, a timestamp can be provided with the image. If CGM data is available for that corresponding time stamp, service 705 is able to use the image data to provide context as to why the CGM data is what it is at a given instance in time. As an example, suppose a user's glucose levels spiked during a particular time period. The embodiments are able to access GPS data to determine where the user was when the spike occurred. As an example, the GPS data may reveal that the user was physically located in an ice cream shop. Based on this location data, the embodiments can infer that the user was likely eating ice cream, hence the spike in blood sugar levels.

Similarly, if the image data reflects a physical exercise or activity performed by the user, the image data can be used to provide context for the user's CGM data. If no CGM data is available during the period corresponding to the time-stamp of the image, service 705 is still able to predict how those activities or food might impact the user's glucose levels. Indeed, the embodiments are able to generate predicted analyte levels based on supplemental data, including GPS data, image data, calendar data, and so on.

Regarding the other sensor data 815, the other sensors can include any kind of step tracker, blood pressure monitor, heart rate monitor, lactate sensor, glucose ketone sensor, glucose ketone alcohol sensor, glucose ketone alcohol lactate sensor, and so on. Indeed, any type of sensor can be used and can provide data. For instance, supplemental data can be fed as input to a health model or profile, and that supplemental data can be obtained from one or more of a glucose ketone sensor, a glucose ketone alcohol sensor, or a glucose ketone alcohol lactate sensor.

Regarding user input data 820, a user can provide supplemental information as to the activities he/she is engaged in and/or the food being consumed. A user can also provide context or information describing why his/her glucose levels are what they are.

Returning to FIG. 7, service 705 then performs analytics on that input data to generate a data model 750. Data model 750 includes profile data 755 for the user, predictions 760 for the user, and recommendations 765 for the user.

Regarding the profile data 755, service 705 is able to generate a profile for a user and monitor that user's historical behavior and trends. As new data is acquired and/or predicted, that data can be included in the user's profile data 755.

Regarding the predictions 760, service 705 is able to predict various aspects related to the user's health, particularly with regard to the user's glucose levels or other analyte levels. Such predictions 760 can occur even when only intermittent data is available. The predictions 760 are based on the user's historical behavior, historical glucose levels (e.g., baseline data, such as perhaps sensor data 605 and 615 from FIG. 6), as well as the supplemental data 745. The predictions 760 can also be based on the real-time collection of data from other sources, such as calendar events (e.g., perhaps a scheduled event to attend a restaurant is detected), GPS data, heart rate data, and so on.

Regarding the recommendations 765, service 705 generates one or more of these recommendations and submits them to the user for consideration. As some non-limiting examples, the recommendations 765 include recommendations to re-attach the sensor (if it is not currently attached); recommendations to use or obtain a new sensor; recommendations on daily health habits (e.g., food intake, exercise, etc.); recommendations on application usage; and so on. For example, service 705 may recommend the user go for a walk while located at an ice cream shop where service detected elevated glucose levels after the user previously visited that location. In this example, service 705 would use the current location of the user and prior glucose data associated with that location.

Figure 9:
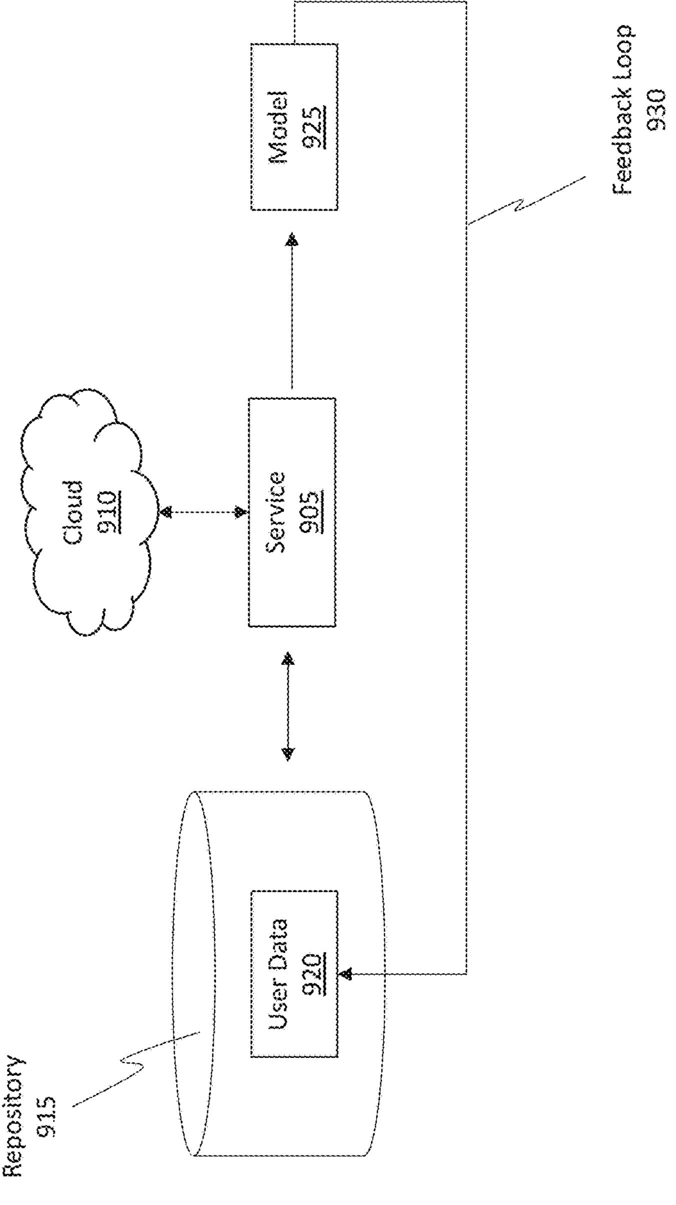
FIG. 9 illustrates how a service can access a repository of user data to perform population matching.

Turning briefly to FIG. 9, FIG. 9 shows an example architecture 900 that includes a service 905, which is representative of the services described thus far. Service 905 can optionally be a cloud 910 service or a service that interacts with the cloud 910. Service 905 is able to access a repository 915 that includes user data 920. User data 920 can be a collective corpus of data describing various attributes of other users. User data 920 can be organized based on different factors, such as age, sex, daily health habits, occupation, height, weight, and so on.

Any given user can have data stored among the user data 920. Service 905 is able to generate a model 925 for a user and compare that model 925 to the other users' data in the repository 915. As new data is learned and entered into the model 925, service 905 can feed that new data back into the repository 915, as shown by feedback loop 930.

Figure 10:
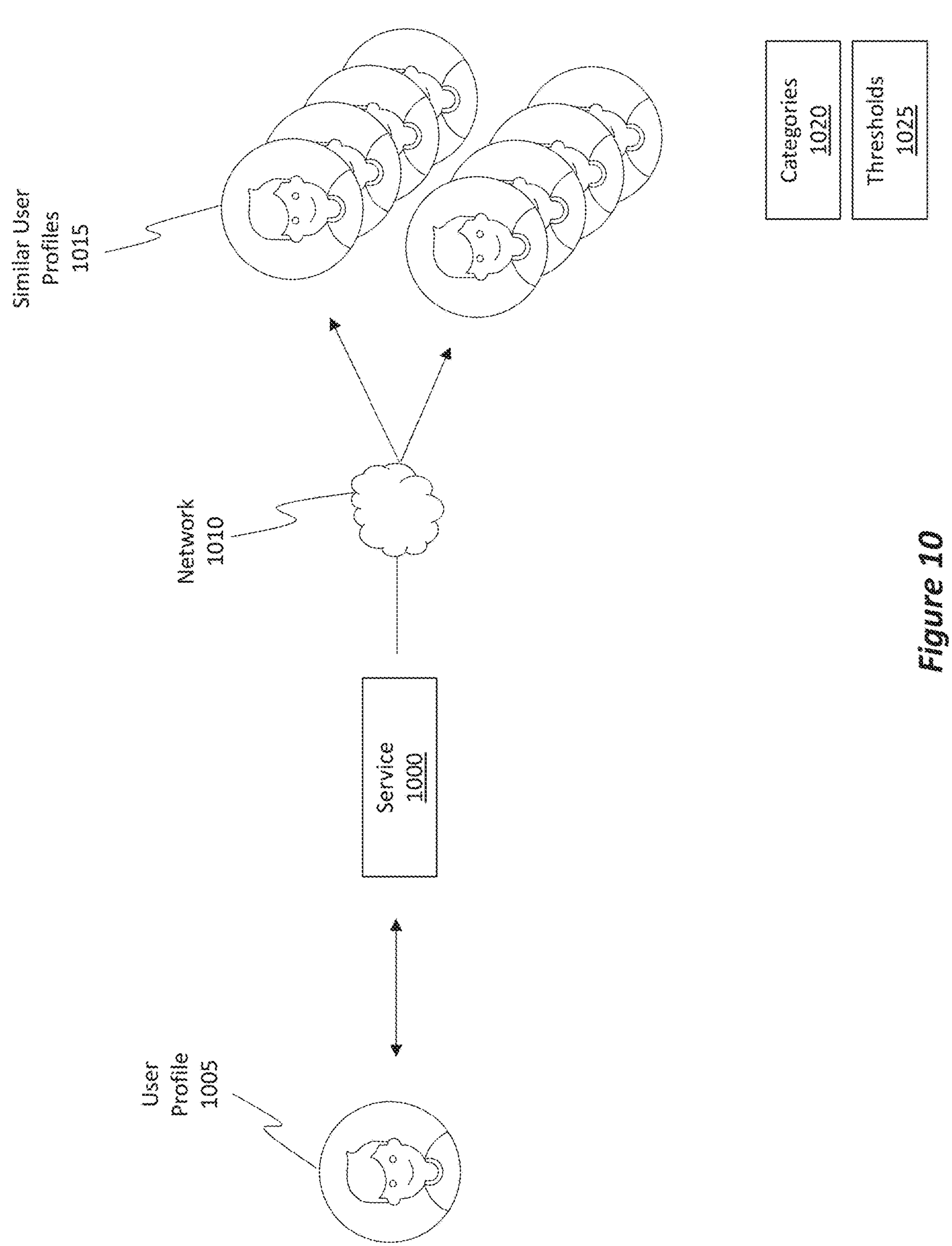
FIG. 10 illustrates how a user can be matched to other users.

FIG. 10 shows a service 1000 that is representative of the services described herein. Service 1000 is able to access a profile of a user, as shown by user profile 1005. Service 1000 can also attempt to identify other users who have profiles that are sufficiently similar to the user profile 1005 using, for example, a network 1010 connection. For example, the similar user profiles 1015 (which may be included in the user data 920 stored in the repository 915 of FIG. 9) are identified as having a threshold number of characteristics that match or that are similar to the user profile 1005. Such characteristics can include age, weight, height, sex, occupation, physical activity level, health issues, and so on.

Accordingly, service 1000 is able to find other user profiles (e.g., other people "like me") that have a number of categories 1020, characteristics, or features that are similar to those included in user profile 1005. If a threshold 1025 number of these categories 1020 are similar to the categories listed in user profile 1005, then service 1000 can learn from those other profiles and optionally generate recommendations or predictions using those other profiles. Therefore, even when discontinuous data is available from a sensor, service 1000 is nevertheless able to generate recommendations based not only on that discontinuous data but also on the data from other users who are identified as being similar to the user. To determine similarity, the embodiments may attempt to match characteristics between users. If a threshold number of characteristics are determined to be matching as between two users, then those two users are determined to be similar to one another. Optionally, a range or buffer can be defined for each characteristic. If the user's value for a characteristic falls within the defined range or buffer with respect to another user's characteristic, then those two users can be viewed as being matched for that characteristic. As another example, the embodiments are able to use other profile data as supplemental baseline data for a particular user. For instance, it may be the case that the embodiments determine that the user's own baseline data is stale. In such a scenario, the embodiments can optionally use another user's data, which is more recent than the user's own baseline data, as the user's baseline data in order to generate prediction data. Optionally, the other user's data can supplement the user's own baseline data.

Stated differently, population matching may be performed to identify one or more other users who share similar characteristics as any given user. By "population matching," it is generally meant that other users are identified, where those other users have a threshold number of characteristics that are within a threshold level of similarity to the current user. As a result, the user is "matched" with other users in the general population. Examples of such similar characteristics include, but certainly are not limited to, one or more of age, sex, height, weight, location, general activity level, or even occupation. For instance, the matched other users can be family members or perhaps even coworkers. The embodiments can also match users with other users who have similar glucose responses to certain inputs. For example, if user A and user B both respond in a similar manner to the same activities and foods, those users can be grouped together. User B's responses can be relied on to then make a prediction for user A when user A does not have an active CGM or has not yet seen a response to a particular food or activity. User B's responses can also be relied on when user A's data is determined to be stale or otherwise not sufficiently reliable. Furthermore, the embodiments are able to identify users who share similar characteristics. For instance, the embodiments can identify users who are of the same age, sex, height, weight, physical activity levels (and so on) and who have similar glucose responses to certain activities or conditions (e.g., when visiting an ice cream shop). As a specific example, the embodiments may rely on another user's data when the current user visits a new ice cream shop. This reliance may be made when the embodiments determine that prior data for that user at that particular location is not available, but that data is available for another user who is "like" the current user. Thus, the embodiments may rely on that other user's data in this instance.

A confidence level can also be generated to reflect the level of confidence that the embodiments have with respect to the supposed match between the current user and the other, matched users. That is, a confidence level can be determined, where that confidence level reflects how close or how similar the user is relative to the other users. Optionally, the ML engine can generate this confidence metric.

Predicted Data

Figure 11:
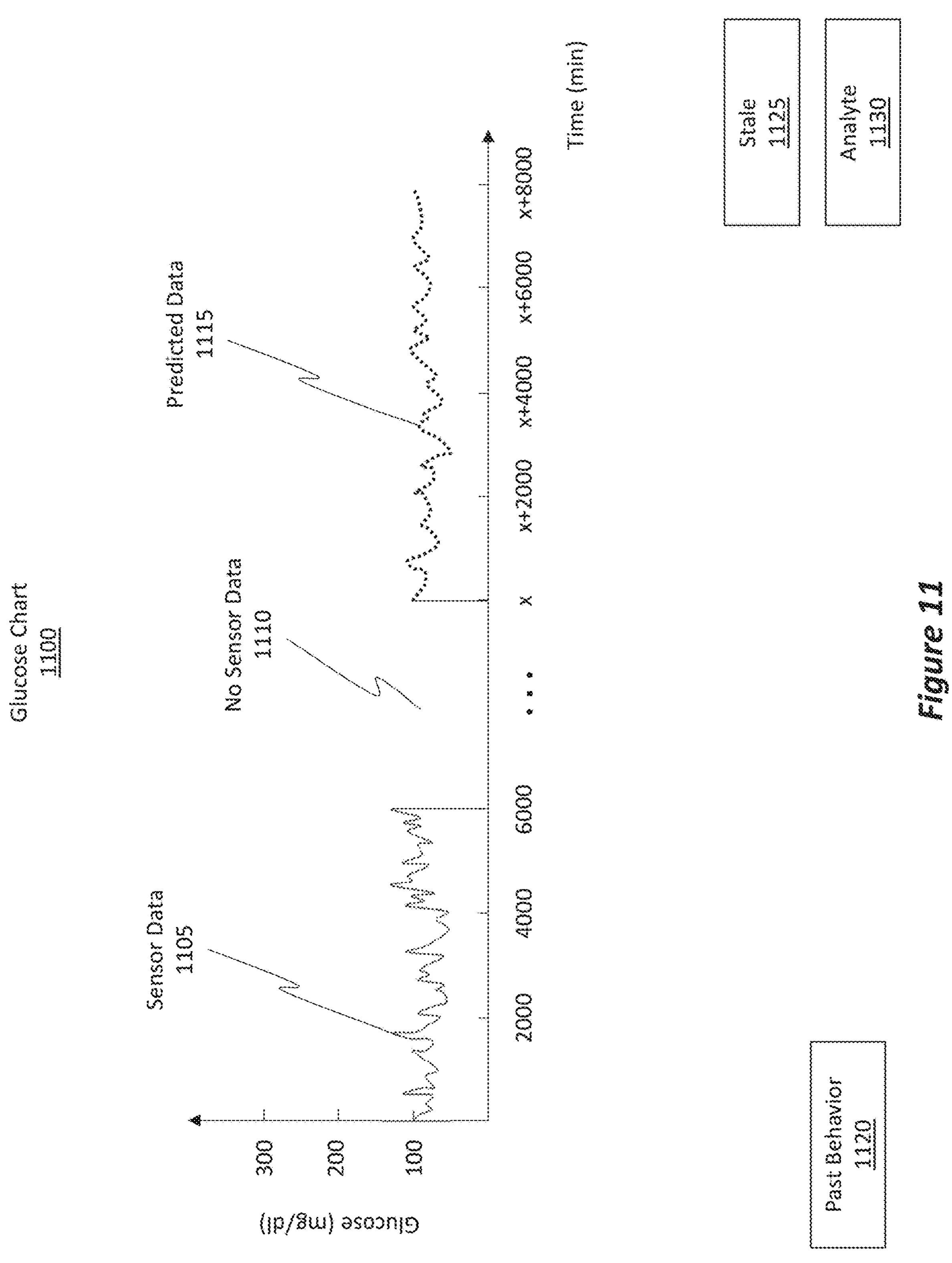
FIG. 11 illustrates how predicted data can be generated based on sparse or intermittent data.

FIG. 11 shows a glucose chart 1100 that includes sensor data 1105 obtained during a first time period. No sensor data 1110 is available between time 6000 and time x. The embodiments (e.g., the disclosed services) are able to detect this time period during which no new sensor data is being obtained. In response to the detection of this time period, the embodiments are triggered to generate predicted analyte data. Optionally, the embodiments may implement a time delay before the predicted data is generated. The time delay can be set to any value, such as any number of minutes, hours, or days.

Therefore, in accordance with the disclosed principles, the embodiments are able to generate predicted data 1115 based on the initial baseline set of data (e.g., sensor data 1105, sensor data 605 and/or 615 from FIG. 6 and/or any of the intermittent data discussed herein). Predicted data 1115 is based on the past behavior 1120 of the user, as documented via the sensor data 1105 and any of the supplemental data described herein. The more data that is included in the baseline set of data, the more trends and patterns can be detected, resulting in an increased likelihood that the predicted data 1115 is accurate. The quality of the predicted data 1115 may deteriorate over time or may deviate. The embodiments may then prompt the user to allow new sensor data to be acquired to ensure the application is providing relevant and useful information to the user.

In some implementations, the embodiments will prompt the user to acquire new sensor data instead of continuing to rely on the predicted data 1115, particularly if a determination is made that the predicted data 1115 is stale or is becoming stale. In one scenario, for predicted data to be or to become "stale," that predicted data may have been used for a prolonged period of time, such as a time period that exceeds a preestablished threshold amount of time since up-to-date sensor data was acquired. In some scenarios, the predicted data may become stale and/or the user's profile, model, or sensor data 1105 may become stale. For instance, the predicted data 1115 may become stale 1125 in its accuracy levels if new sensor data has not been received for a prolonged period of time (e.g., a time period beyond a threshold time period). For instance, the accuracy of the predicted data 1115 may trend or deviate toward an inaccurate result if new sensor data is not received within a time period so as to re-calibrate the predicted data 1115. Accordingly, some embodiments determine that the predicted response data (e.g., predicted physiological data or predicted analyte data) is stale or is in need of an update. The embodiments can then submit a recommendation to the user to facilitate one or more of: acquiring new sensor data from an existing sensor or acquiring new sensor data from a new sensor. It should also be noted how the sensor data 1105 can be referred to as analyte 1130 data and how the predicted data 1115 can be referred to as predicted analyte data.

In some embodiments, predicted data that is displayed in a chart or graph can be displayed differently than actual sensor data displayed in that same graph. Doing so allows a user to easily distinguish between sensor data and predicted data. Any technique can be used to provide a distinction. For instance, different colors, line thickness, dotting, and so on can be used to differentiate the two types of chart data.

App Features

Figure 12:
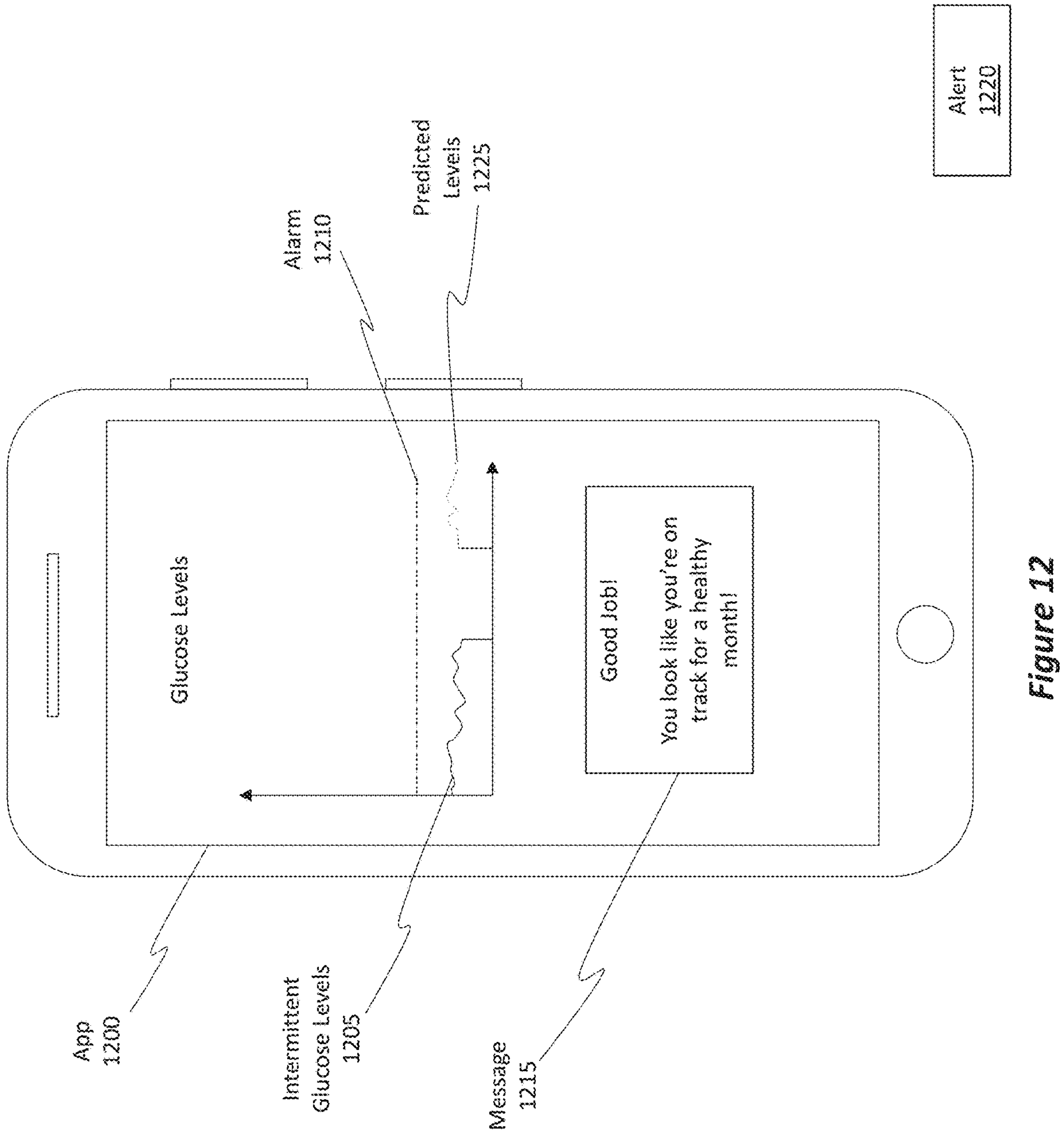
FIGS. 12, 13A, 13B, 14, 15, and 16 illustrate various different user interfaces of an application.

FIG. 12 shows an example app 1200 that can be provided by the disclosed services. In this example scenario, app 1200 shows the glucose levels for a user collected over a period of time, as reflected by the intermittent glucose levels 1205. Notice, the sensor data stops at some point in, such as perhaps because the user stopped wearing the sensor. App 1200 also includes an option to set an alarm 1210, which can be used to inform the user if his/her glucose levels exceed the alarm threshold 1210. In other examples, an alarm threshold can be set for a low glucose event in which the user's glucose levels fall below a low threshold, lower than threshold 1210.

App 1200 also includes a user interface (UI) element for displaying a message 1215. This message 1215 can operate as an alert 1220 to the user. In some cases, the alert 1220 can inform the user that he/she should start wearing the sensor again in order to collect updated sensor data. In some examples, message 1215 can display coaching messages or insights as described below.

Optionally, the embodiments can determine a frequency at which to transmit the alert to the user. In some scenarios, this alert can be one that recommends the user assist in obtaining new or updated sensor data. The frequency may optionally be based on one or more characteristics of the user. For instance, the characteristics can include a pattern by which the user uses the sensor, a pattern by which the user performs various activities, or a pattern by which the user consumes various foods.

App 1200 also shows various predicted levels 1225 for the user. The display of these predicted level 1225 may have been triggered in response to the device not receiving updated data for a determined time period. The predicted levels 1225 are predicted based on the user's historical levels and, potentially other profile information. In some implementations, the display of the predicted levels 1225 is caused to be different than the display of the actual sensor data (e.g., the intermittent glucose levels 1205). For instance, the predicted levels 1225 can be displayed using dotted lines, different coloring, bolded lines, flashing lines, or any other visual emphasis so as to distinguish the predicted levels 1225 from the actual sensor data. In some cases, app 1200 may not display predicted glucose levels 1225; rather, app 1200 may provide insights based on the intermittent glucose levels 1205.

Figure 13A:
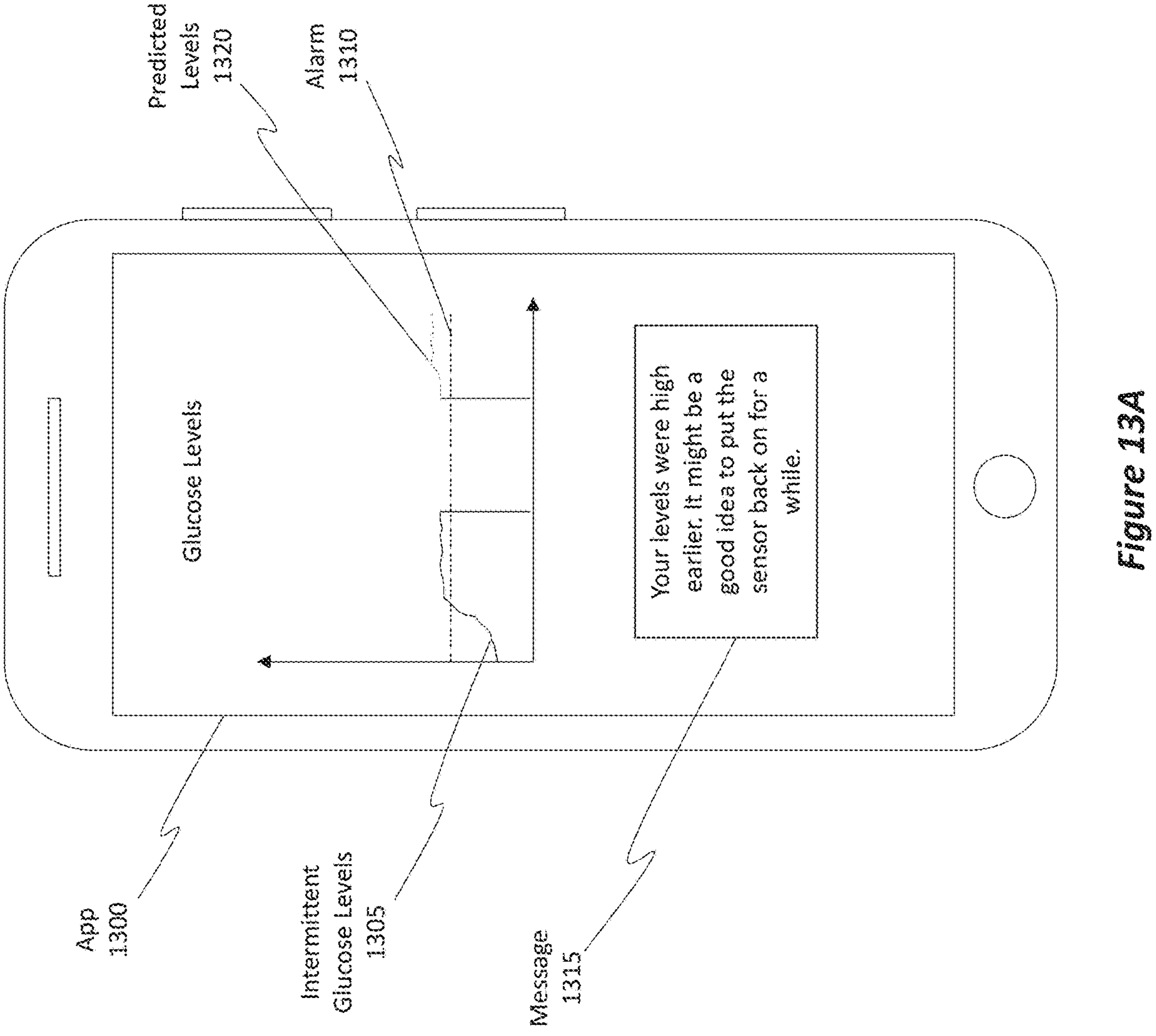
Figure 13B:
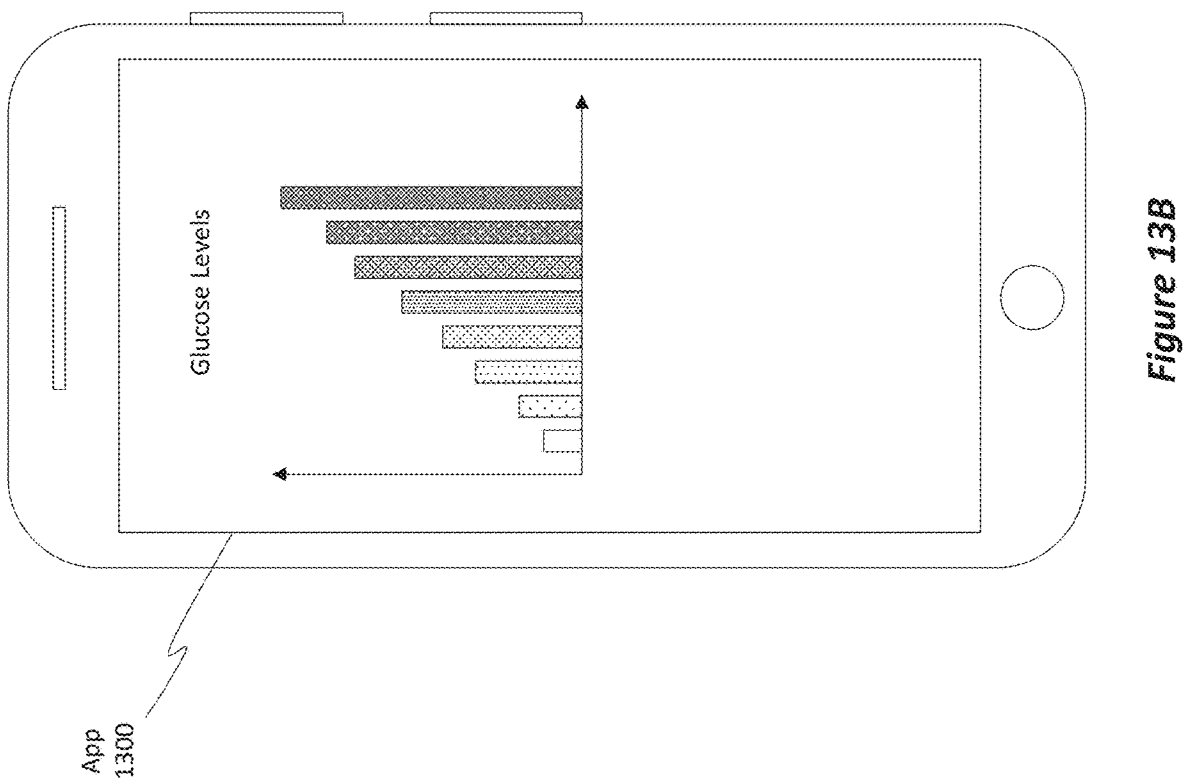

FIG. 13A illustrates an app 1300 that shows intermittent glucose levels 1305, an adjustable alarm 1310, a message 1315, and predicted levels 1320. In this example, the user's intermittent glucose levels 1305 and even the predicted levels 1320 are shown as exceeding the alarm 1310 level. As a result, the message 1315 is displaying language intended to help the user reduce his/her glucose levels by better monitoring those levels via the sensor. In this example scenario, message 1315 tells the user that he/she should reattach the sensor. FIG. 13B shows another example user interface of the app 1300. FIG. 13B includes a simplified depiction of glucose levels using bar charts that can optionally have various different colors, color ranges, shadings, and so on.

Figure 14:
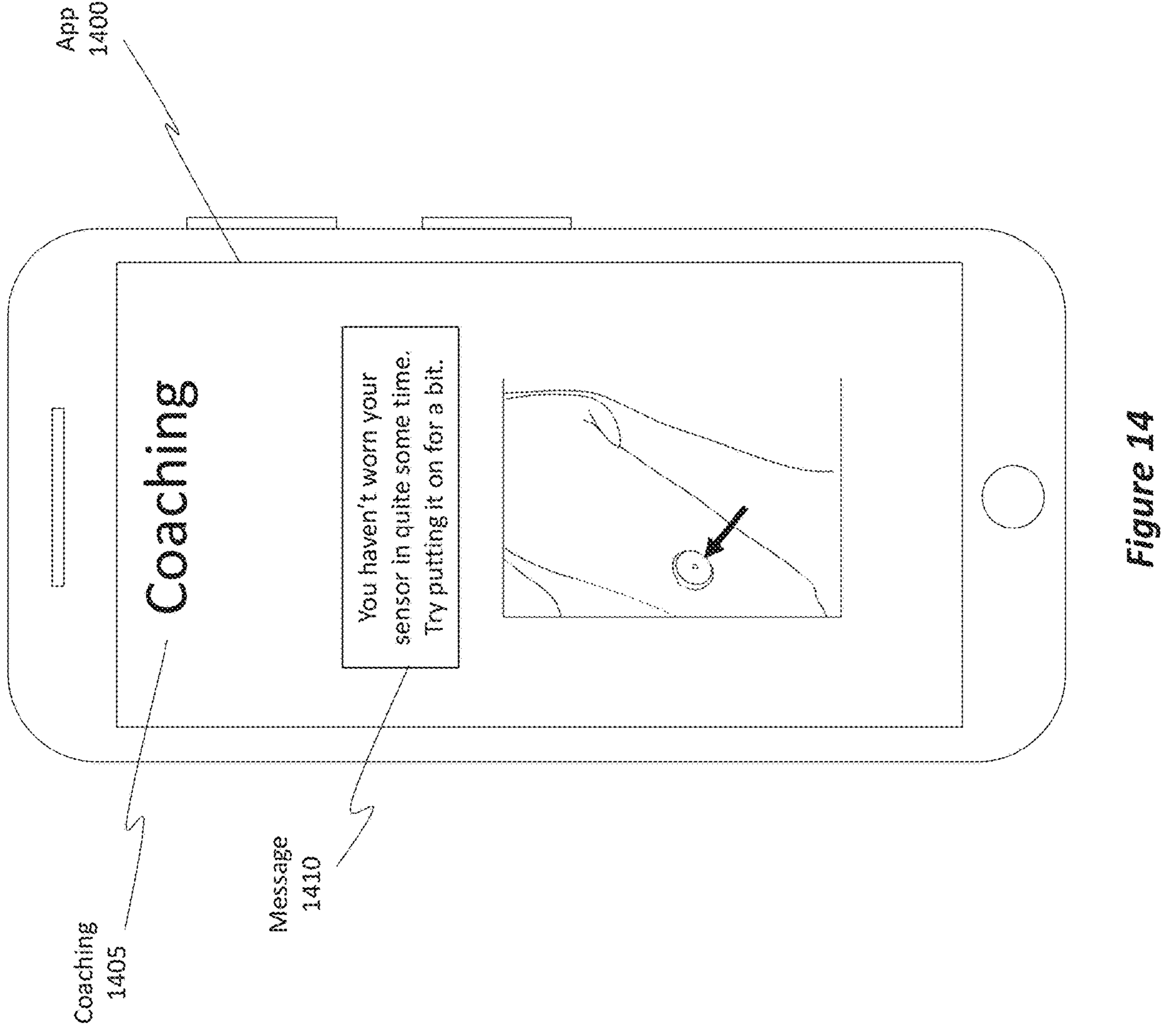

FIG. 14 shows an app 1400 that is providing coaching 1405 to a user via various different messages, such as message 1410. The content shown in FIG. 14 can be displayed simultaneously with or separately from the predicted levels mentioned earlier. For instance, message 1410 encourages the user to re-attach the sensor so new data can be collected. Other coaching messages can also be provided, such as encouragement on what foods to eat, what physical activities to perform, and so on. With regard to encouragement, the embodiments can display messages recommending certain foods that may help to lower or perhaps raise glucose levels. The embodiments can also display messages recommending specific physical activities to perform, how long, what intensity, and/or when to perform those activities. While an activity is being performed, coaching or encouragement can also be provided to the user. In some cases, this encouragement can be in the form of audio output, video output, text output, or image output. Thus, some embodiments provide a coaching prompt to the user during various time periods, even during times when sensor data is not being provided from a sensor. Instead, during such a time period, the embodiments may be generating predicted data. Messages reflecting the content mentioned above can be displayed as message 1215 from FIG. 12.

Figure 15:
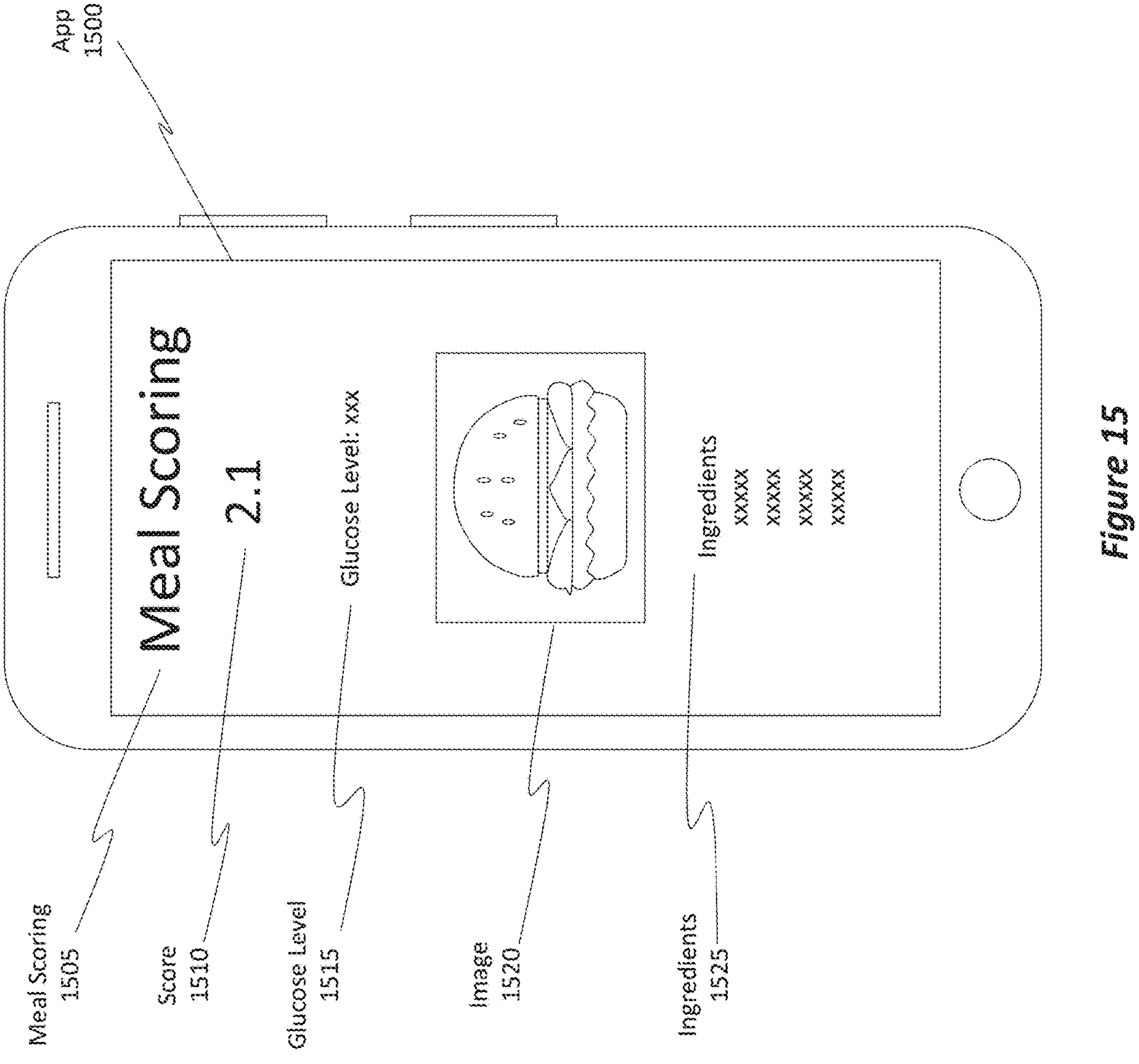

FIG. 15 shows an example app 1500 that includes a meal scoring 1505 feature. This feature displays a score 1510 to the user, where that score 1510 ranks the user's food choices in terms of contributing to the user's overall health or, in particular, to the user's glucose levels. App 1500 can optionally display the user's glucose level 1515.

Different data can be used to generate the score 1510. In some implementations, the user can take a picture of the food being consumed, and that picture can be uploaded to the app 1500, as shown by image 1520. Object recognition can be performed on the image 1520 to determine what ingredients 1525 are included in the food and what the nutritional details of the food are likely to be. Score 1510 can be based on these estimates. In some cases, score 1510 can also be based on community data (e.g., the people like me scenario mentioned earlier), such as data from the similar user profiles 1015 of FIG. 10.

In some cases, the user can enter input on the food. Such input can include the type of food, the portion size, the ingredients list, and so on. Input from another application can also be used. As one example, food calorie data or food macro data can be used as input.

Figure 16:
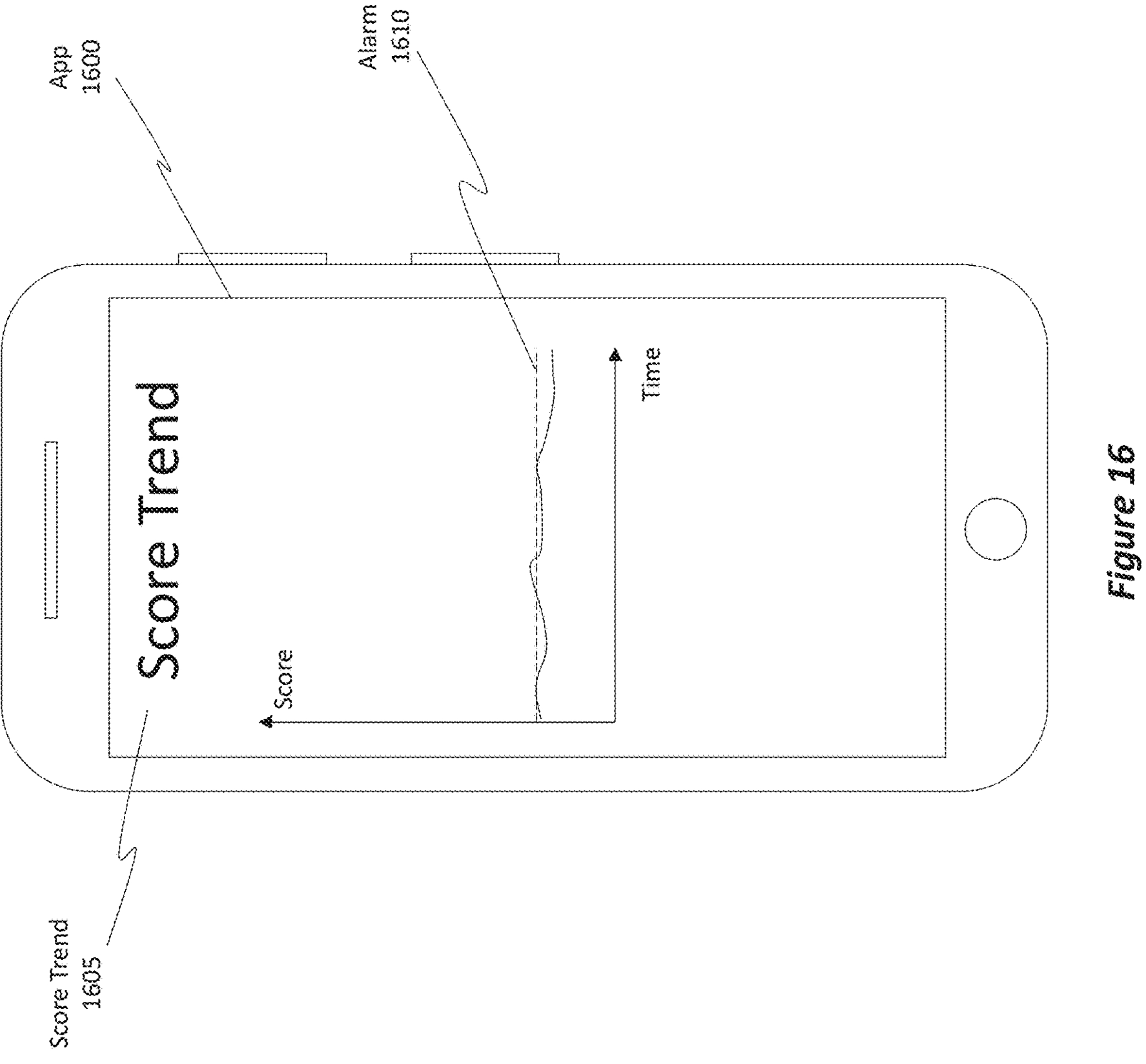

FIG. 16 illustrates an example app 1600 showing a score trend 1605 for the user. In this example scenario, app 1600 plots the user's scores (e.g., score 1510 from FIG. 15) over time.

In some implementations, the user can define an alarm 1610. If the user's score exceeds the limit set by the alarm 1610, then a message or other alert can be provided to the user indicating such.

Example Methods

The following discussion now refers to a number of methods and method acts that may be performed. Although the method acts may be discussed in a certain order or illustrated in a flow chart as occurring in a particular order, no particular ordering is required unless specifically stated, or required because an act is dependent on another act being completed prior to the act being performed.

Figure 17:
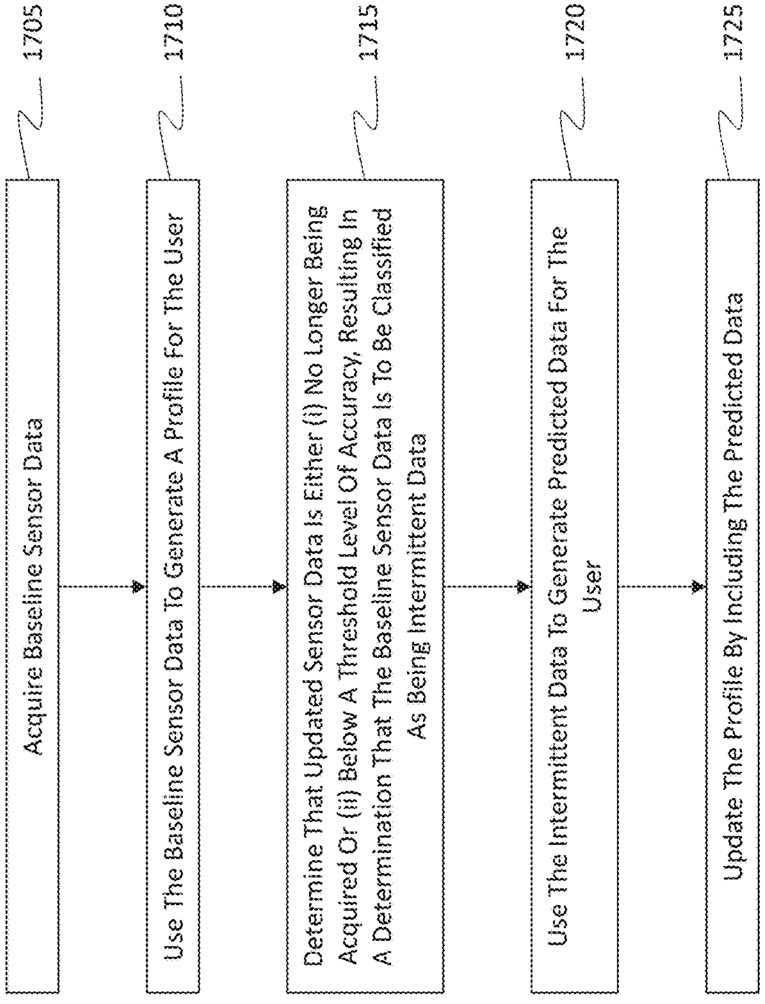
FIGS. 17 and 18 illustrate flowcharts of example methods for predicting analyte data based on intermittent data.

Attention will now be directed to FIG. 17, which illustrates a flowchart of an example method 1700 for generating a glucose level profile (aka a "health profile" or "health model") for a user, where the glucose level profile is based on intermittent (aka "sparse" or "periodic") baseline glucose data (or sparse sensor data) received from a CGM sensor (or any type of invasive or non-invasive sensor) and where the glucose level profile includes predicted glucose data that is predicted from the intermittent/sparse baseline glucose data. Method 1700 can be implemented by any of the services described herein, and in particular by service 705 of FIG. 7.

Method 1700 includes acquiring baseline sensor data from a CGM sensor (act 1705). The baseline sensor data reflects glucose levels of a user who is wearing the CGM sensor. The baseline sensor data is collected over a first time period. Any time period can be defined.

Method 1700 uses the baseline sensor data to generate a profile for the user (at 1710). The profile tracks the glucose levels of the user throughout the first time period. In addition to the baseline sensor data, additional supplemental data can also be used. Also, the profiled can be generated via known machine learning techniques (e.g., unsupervised learning, supervised learning, semi-supervised learning, reinformed learning, clustering, classification, regression, decision tree, neural networks, anomaly detection).

During a second time period that is subsequent to the first time period, method 1700 determines that updated sensor data is either (i) no longer being acquired from the CGM sensor or (ii) below a threshold level of accuracy, resulting in a determination that the baseline sensor data is to be classified as being intermittent/sparse glucose data (at 1715). Regarding the accuracy level, it may be the case that the sensor is producing data, but perhaps the sensor is not affixed properly to the user. The resulting data may then be skewed or significantly out of a normal range. Consequently, the embodiments may determine that the accuracy level of the data is below an established threshold, and the embodiments may refrain from relying on that data.

In response to that determination, method 1700 uses the intermittent/sparse glucose data to generate predicted glucose level data for the user (act 1720). The predicted glucose level data is reflective of predicted glucose levels for the user during the second time period. Stated differently, the sparse sensor data (e.g., sensor data 605 and 625 from FIG. 6) and supplemental data (e.g., supplemental data 745 from FIG. 7) can be used to generate predicted physiological response data for the user. This predicted physiological response data is reflective of a predicted physiological response for the user during the second time period. Optionally, a determination is made that the user is not wearing the analyte sensor during the second time period.

Method 1700 then includes updating the profile by including the predicted glucose level data and/or the predicted physiological response data (act 1725). Updating the profile can be performed by adding the data to a database associated with the user. In some cases, this process can also involve using data from other users who are determined to be similar to the current user.

Later, new sensor data may be acquired. Optionally, the new sensor data can be used to re-calibrate or adjust the predicted data. Optionally, the new sensor data can also be used to tune future generation of predicted data. In some cases, additional data (e.g., second sensor data) can also be acquired and can be used to fine tune the prediction. Stated differently, during a third time period that is subsequent to the second time period, the embodiments can acquire second sensor data from a second CGM sensor worn by the user. The embodiments can then update the profile by including the second sensor data.

In some implementations, the profile is updated via a machine learning engine. Also, the service can be implemented either on a local client device or in a cloud environment.

In some scenarios, the second CGM sensor is different than the first CGM sensor. In other scenarios, the second CGM sensor is the same as the first CGM sensor.

A machine learning engine can analyze the second sensor data. The machine learning engine may include analytics on the first sensor data, the predicted glucose level data, and/or the second sensor data in the profile. The machine learning engine, which can update the profile, may also be included as a part of the service. In some cases, the service and the machine learning engine, which can update the profile, may be included in a same computing architecture.

Figure 18:
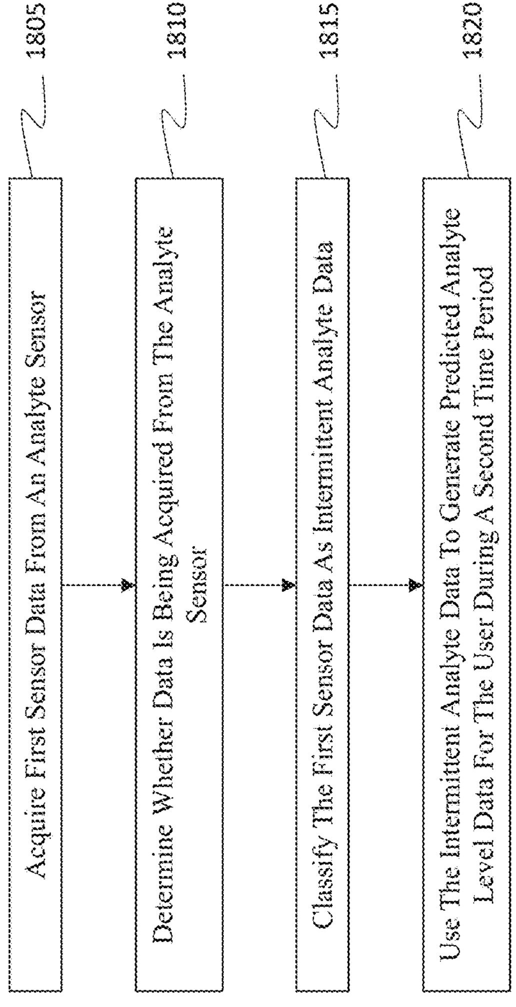
Figure 18:
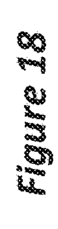

FIG. 18 illustrates a flowchart of an example method 1800 for predicting analyte levels and for generating a health model for a user. Method 1800 can also be implemented by the disclosed service, such as service 705 of FIG. 7. That service can optionally be a cloud service.

Method 1800 includes acquiring first sensor data (e.g., sensor data 605 from FIG. 6) from an analyte sensor (e.g., sensor 730 of FIG. 7) (act 1805). The first sensor data can include a plethora of data. For instance, the data can be obtained from more than one sensor worn continuously (e.g., one after the other, with no more than 24 hours between sensors). The first sensor data reflects analyte levels of a user who is wearing the analyte sensor, and the first sensor data is collected over a first time period. Stated differently, the first sensor data reflects a physiological response of the user. The first time period can be set to any duration of time. As various examples, the first time period can be at least 10 contiguous days or perhaps at least 14 contiguous days. The time period can be a set number of hours, days, or even months. The time period can be a contiguous time period or a noncontiguous time period, such as the aggregation of multiple discrete units of time over an overall period of time. In some scenarios, the first time period is one week or greater. In some scenarios, the first time period is about one month. The first time period can be between about one month and about six months.

Optionally, method 1800 can include an act of using the first sensor data to generate a profile or health model for the user. This profile/health model tracks the analyte levels (or physiological responses, such as glucose levels) of the user throughout the first time period. The profile can include information relating to meals the user has consumed. The profile can also track glucose levels for the same meal that has repeatedly or previously been consumed by the user. Consequently, the profile may include a trend of glucose levels for that meal. In some scenarios, the profile includes glucose level trends for different meals the user has consumed, and the profile includes information relating to a comparison between the different meals. The model or profile can be updated using new sensor data obtained during a subsequent time period. For instance, a first time period may involve the collection of sensor data. A second time period, which is subsequent to the first time period, may involve the generation of predicted data because no up-to-date sensor data is available during the second time period. A third time period, which is subsequent to the second time period, may then again involve the collection of sensor data.

Method 1800 includes determining whether data is still being acquired from the analyte sensor (act 1810). In some cases, the embodiments rely on a threshold time period to avoid scenarios where a small gap in time triggers a prediction event. For instance, if sensor data is not acquired for a brief time period, the embodiments may refrain from triggering the prediction techniques. On the other hand, if sensor data is not obtained for a prolonged time period (e.g., longer than an established time threshold), then the embodiments may trigger the prediction techniques. If sensor data is not acquired for a determined time period, then a second time period is identified as commencing. The second time period is subsequent to the first time period. The embodiments can determine that sensor data is no longer being acquired from the analyte sensor, thereby resulting in the first sensor data being "discontinuous," "intermittent," "sparse," or "periodic" analyte data (or physiological data).

Upon a determination that data is no longer being acquired from the analyte sensor, method 1800 includes classifying the first sensor data as intermittent or discontinuous analyte data (act 1815).

Method 1800 includes using the intermittent/discontinuous/periodic analyte data to generate predicted analyte level data (or predicted physiological response data) for the user during the second time period (act 1820). The predicted analyte level data is reflective of the intermittent analyte data. The profile can then be updated by including, in the profile, the predicted analyte level data (or predicted physiological response data).

Optionally, an ML algorithm, which may be used to generate the user's profile, may be trained based on analyte training data (e.g., unsupervised learning, supervised learning, semi-supervised learning, reinformed learning, clustering, classification, regression, decision tree, neural networks, anomaly detection). Stated differently, the embodiments can train the ML algorithm based on the discontinuous analyte data. This ML algorithm can be used to generate the predicted analyte level data.

In some implementations, the intermittent analyte data is compared against a repository of baseline sensor data for other users. For instance, the repository can include a plethora of information about other users, such as perhaps those users' profile data. The user's analyte data can be compared and contrasted to the other users' data to determine how closely the user's data tracks with the other users' data.

As an example, the other user's data can be analyzed to determine an average trend. The user's data can then be compared against that average trend to determine how the user is in comparison to an "average" person.

In some cases, the generated trend data can be more granularly defined. For instance, the trend data can be generated for a person having similar characteristics as the user (e.g., age, weight, height, sex, etc.). Optionally, the predicted analyte level data can be compared against trending data of other users. As another example, some embodiments determine a standard population trend for multiple other users and then compare the profile of the user against the standard population trend. In some cases, the standard population trend is determined by aggregating or collecting data from many different users. An analysis can then be performed on that data to detect clusters, trends, or patterns in the data. These trends may be used to define average ranges or values for specific behaviors or responses in a person. Thus, trending data can be determined, and the trending data can be used to define normalized responses.

In some embodiments, the profile may include glucose trend levels for different users who all consumed a same or similar meal. In some cases, the profile may include supplemental information that is relied on to generate the predicted analyte level data. The profile can also be compared against profiles of other users who are in the same demographic group. In some implementations, the embodiments use the profile of the user to determine a behavioral trend for the user. The embodiments may then perform one or more of (i) recommending a behavior change to the user or (ii) prompting the user for additional sensor data.

In some implementations, the predicted analyte level data is compared against metadata associated with the user. As an example, the metadata can include one or more of a past glucose level data for the user, location(s) of the user (e.g., certain glucose level peaks or valleys may be correlated with specific locations the user is at), food consumed, information obtained from a food delivery application, physical activity, or date and time.

In some cases, the embodiments can acquire new sensor data from one of the analyte sensor or a new analyte sensor (e.g., a second analyte sensor). For instance, the embodiments can submit a recommendation to the user to either re-attach the sensor or to obtain and use a new sensor. New sensor data can then be acquired. That is, method 1800 can further include an act of prompting the user to put either the analyte sensor or a new analyte sensor on to acquire new data. Optionally, the application or service can detect the second analyte sensor via a connection or pairing request. The profile can also be updated using data obtained from the second analyte sensor.

In some scenarios, the profile includes trend data reflecting how the user's body is becoming more insulin resistant. Supplemental data can also be added to the profile. This supplemental data may include data from a hemoglobin A1C test. As the user becomes more insulin resistant, the embodiments can provide updated recommendations to avoid certain foods or to engage in certain activities.

Optionally, method 1800 includes an act of receiving user input. This user input supplements the discontinuous analyte data. The user input provides a context for at least some of the discontinuous analyte data. Optionally, method 1800 includes an act of generating a meal score for a meal the user has consumed. The meal score may be based on glucose level data collected during a time range after the meal was consumed by the user. The meal score may also be based on one or more of a meal portion size, a meal type, or a listing of ingredients. In some scenarios, the meal score is based on an uploaded photograph of the meal. The meal score can also be based on manual input or data obtained from a different application. Optionally, the user can continue to enter supplemental data (e.g., meal and exercise data) via the application when that user is not wearing an active sensor.

In some implementations, the profile includes an estimation as to a health level of the meal based on prior meals of a same type as the meal. The profile may also include an estimation as to a health level of the meal based on how other users having similar profile characteristics as the user responded to the meal.

As an example, method 1800 may include an act of identifying a different user who shares similar profile characteristics as the user. The embodiments then determine that the different user is or has previously consumed a meal similar to a meal the user is or will consume. The embodiments use meal-specific analyte levels of the different user to predict meal-specific analyte levels for the user for said meal.

In some scenarios, the profile includes glucose fingerprints for the user for different meals. By "fingerprint," it is generally meant that the profile tracks information for the meal and is able to retain and query that information at a later instance in time.

In some example scenarios, the embodiments facilitate peer to peer sharing of sensor data. For instance, the sensor data can be stored in the repository mentioned earlier and be made accessible to the various user devices (i.e., peers). The embodiments can then identify users who share physiological response characteristics or other physiological characteristics that are similar to the user. Optionally, user data can be anonymized or otherwise de-identified with respect to user identity. Despite user data being anonymous, various consultations can still be performed to group users together so as to have a large corpus of data for related users.

The embodiments can also access one of a calendar or a GPS data to acquire supplemental data about the user. This supplemental data is then associated with the periodic sensor data using time information or time-based information. The supplemental data provides context for at least a portion of the periodic sensor data.

Some embodiments determine that the predicted physiological response data is stale. For instance, to be "stale," the time since actual sensor data was collected may have exceeded a threshold time period. As a result, the predicted data has been relied on for a prolonged time period, and it may be the case that the predicted data has deviated or is otherwise uncalibrated. In view of the predicted data now being stale, the embodiments are able to submit a recommendation to the user to facilitate one or more of: acquiring new sensor data or prompting the user to use a different analyte sensor. In any event, the embodiments attempt to influence the user to use a sensor so that updated sensor data can be acquired. Consequently, the predicted physiological response data may be determined to be stale after a determined time period has elapsed with no new data from the analyte sensor.

In one example implementation, an intermittent use case can involve athletes. For instance, an athlete may acquire glucose measurements only during a period of physical activity (e.g., during a run, triathlon, competition, tennis match, or any other physical activity), and it might be the case that a high level of accuracy is not required. Thus, the athlete may use an analyte sensor only when actively performing a physical activity (e.g., competing, training). In some examples, the athlete may use a glucose sensor during a first period leading up to a physical activity, a second period during the physical activity, and a third period following the physical activity. The embodiments are able to rely on other supplemental sensor data, such as accelerometer or footwear contact sensors to supplement analyte data. In this way, the system can use such other supplemental data as a proxy for glucose information during physical activity in which the user is not wearing an analyte sensor (in accordance with the embodiments described herein). The other sensor information can also be used to identify the first period leading up to the physical activity, the second period during the physical activity, and/or the third period following the physical activity.

In other examples, an athlete may wish to use a sensor during longer periods of time such that he or she may compare his analyte information between any of periods of physical activity, periods preceding physical activity, periods following physical activity, and/or periods of no (or little) physical activity. In this way, the system can help the user understand how physical activity (including timing, intensity, duration, and activity type) influences their analyte levels and, conversely, how their analyte levels influence their physical activity/performance and/or recovery. This information can help the athlete determine preferred meals and/or supplements (including timing and/or portion(s) of such meals and/or supplements) to help improve performance and/or recovery. In some examples, the system can recommend meals/snacks and/or supplements to help support physical activity based on prior and/or current supplemental information (e.g., meal/snack and/or supplement information, supplemental sensor data) and/or analyte sensor data.

The embodiments can also notify the athlete to remember to put on a sensor (e.g., based on calendar information showing an upcoming planned physical activity, based on other sensor data (e.g., accelerometer or footwear contact sensors) showing physical activity).

In some cases, the prescribed intermittent use of a sensor may also encourage the next use of that sensor. As more data is collected, improved prediction results can also be generated.

Accordingly, the disclosed embodiments provide numerous benefits to how sensor data is analyzed and used. The embodiments are beneficially configured to operate particularly when faced with a scenario where sparse, intermittent, or periodic sensor data is available.

Some embodiments are able to use blood glucose data obtained via other techniques. For example, a finger stick or prick tool can be used to obtain a sample to determine the blood glucose data. Thus, even if a user is not wearing a sensor, the user's blood glucose data can still be obtained. This blood glucose data can help keep the CGM-based model from becoming stale. In other words, this data can be used to extend the life of the model.

Example Computer/Computer Systems

Figure 19:
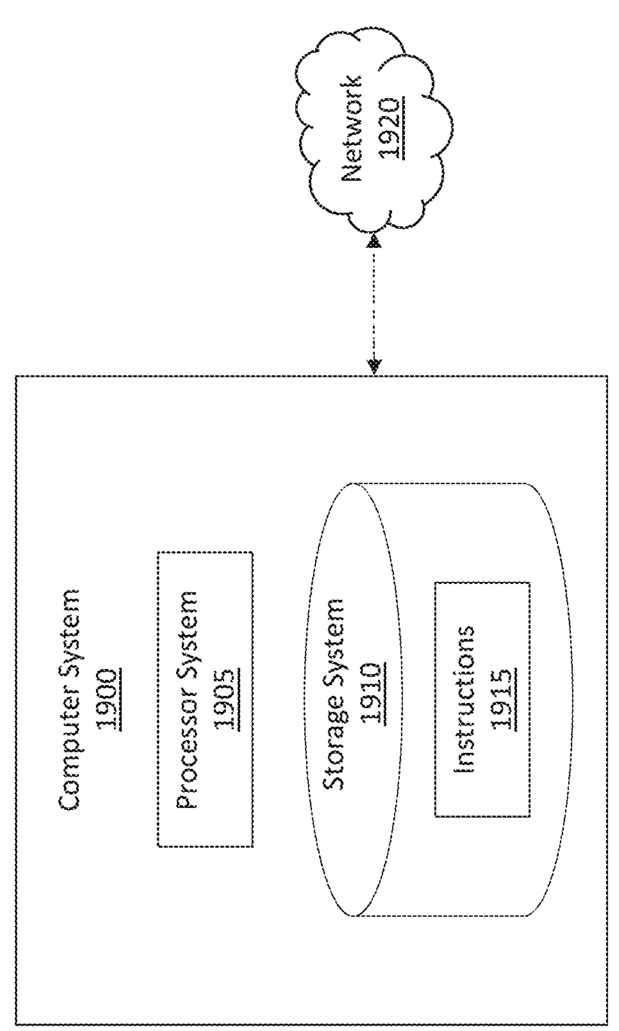
FIG. 19 illustrates an example computer system that can perform any of the disclosed operations.

Attention will now be directed to FIG. 19 which illustrates an example computer system 1900 that may include and/or be used to perform any of the operations described herein. For instance, computer system 1900 can implement any of the services described herein.

Computer system 1900 may take various different forms. For example, computer system 1900 may be embodied as a tablet, a desktop, a laptop, a mobile device, or a standalone device, such as those described throughout this disclosure. Computer system 1900 may also be a distributed system that includes one or more connected computing components/devices that are in communication with computer system 1900.

In its most basic configuration, computer system 1900 includes various different components. FIG. 19 shows that computer system 1900 includes a processor system 1905 that includes one or more processors (aka a "hardware processing unit") and a storage system 1910.

Regarding the processor(s) of the processor system 1905, it will be appreciated that the functionality described herein can be performed, at least in part, by one or more hardware logic components. For example, and without limitation, illustrative types of hardware logic components/processors that can be used include Field-Programmable Gate Arrays ("FPGA"), Program-Specific or Application-Specific Integrated Circuits ("ASIC"), Program-Specific Standard Products ("ASSP"), System-On-A-Chip Systems ("SOC"), Complex Programmable Logic Devices ("CPLD"), Central Processing Units ("CPU"), Graphical Processing Units ("GPU"), or any other type of programmable hardware.

As used herein, the terms "executable module," "executable component," "component," "module," "service," or "engine" can refer to hardware processing units or to software objects, routines, or methods that may be executed on computer system 1900. The different components, modules, engines, and services described herein may be implemented as objects or processors that execute on computer system 1900 (e.g. as separate threads).

Storage system 1910 may be physical system memory, which may be volatile, non-volatile, or some combination of the two. The term "memory" may also be used herein to refer to non-volatile mass storage such as physical storage media. If computer system 1900 is distributed, the processing, memory, and/or storage capability may be distributed as well.

Storage system 1910 is shown as including executable instructions 1915. The executable instructions 1915 represent instructions that are executable by the processor(s) of the processor system 1905 to perform the disclosed operations, such as those described in the various methods.

The disclosed embodiments may comprise or utilize a special-purpose or general-purpose computer including computer hardware, such as, for example, one or more processors and system memory, as discussed in greater detail below. Embodiments also include physical and other computer-readable media for carrying or storing computer-executable instructions and/or data structures. Such computer-readable media can be any available media that can be accessed by a general-purpose or special-purpose computer system. Computer-readable media that store computer-executable instructions in the form of data are "physical computer storage media" or a "hardware storage device." Furthermore, computer-readable storage media, which includes physical computer storage media and hardware storage devices, exclude signals, carrier waves, and propagating signals. On the other hand, computer-readable media that carry computer-executable instructions are "transmission media" and include signals, carrier waves, and propagating signals. Thus, by way of example and not limitation, the current embodiments can comprise at least two distinctly different kinds of computer-readable media: computer storage media and transmission media.

Computer storage media (aka "hardware storage device") are computer-readable hardware storage devices, such as RAM, ROM, EEPROM, CD-ROM, solid state drives ("SSD") that are based on RAM, Flash memory, phase-change memory ("PCM"), or other types of memory, or other optical disk storage, magnetic disk storage or other magnetic storage devices, or any other medium that can be used to store desired program code means in the form of computer-executable instructions, data, or data structures and that can be accessed by a general-purpose or special-purpose computer.

Computer system 1900 may also be connected (via a wired or wireless connection) to external sensors (e.g., one or more remote cameras) or devices via a network 1920. For example, computer system 1900 can communicate with any number devices or cloud services to obtain or process data.

In some cases, network 1920 may itself be a cloud network. Furthermore, computer system 1900 may also be connected through one or more wired or wireless networks to remote/separate computer systems(s) that are configured to perform any of the processing described with regard to computer system 1900.

A "network," like network 1920, is defined as one or more data links and/or data switches that enable the transport of electronic data between computer systems, modules, and/or other electronic devices. When information is transferred, or provided, over a network (either hardwired, wireless, or a combination of hardwired and wireless) to a computer, the computer properly views the connection as a transmission medium. Computer system 1900 will include one or more communication channels that are used to communicate with the network 1920. Transmissions media include a network that can be used to carry data or desired program code means in the form of computer-executable instructions or in the form of data structures. Further, these computer-executable instructions can be accessed by a general-purpose or special-purpose computer. Combinations of the above should also be included within the scope of computer-readable media.

Upon reaching various computer system components, program code means in the form of computer-executable instructions or data structures can be transferred automatically from transmission media to computer storage media (or vice versa). For example, computer-executable instructions or data structures received over a network or data link can be buffered in RAM within a network interface module (e.g., a network interface card or "NIC") and then eventually transferred to computer system RAM and/or to less volatile computer storage media at a computer system. Thus, it should be understood that computer storage media can be included in computer system components that also (or even primarily) utilize transmission media.

Computer-executable (or computer-interpretable) instructions comprise, for example, instructions that cause a general-purpose computer, special-purpose computer, or special-purpose processing device to perform a certain function or group of functions. The computer-executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the embodiments may be practiced in network computing environments with many types of computer system configurations, including personal computers, desktop computers, laptop computers, message processors, hand-held devices, multi-processor systems, microprocessor-based or programmable consumer electronics, network PCs, minicomputers, mainframe computers, mobile telephones, PDAs, pagers, routers, switches, and the like. The embodiments may also be practiced in distributed system environments where local and remote computer systems that are linked (either by hardwired data links, wireless data links, or by a combination of hardwired and wireless data links) through a network each perform tasks (e.g. cloud computing, cloud services and the like). In a distributed system environment, program modules may be located in both local and remote memory storage devices.

The present invention may be embodied in other specific forms without departing from its characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The present invention can also be described in accordance with the following numbered clauses.

1. A computer system that predicts analyte levels, the computer system comprising: a processor system; and a storage system comprising instructions that are executable by the processor system to cause the computer system to: acquire first sensor data from a first analyte sensor, wherein the first sensor data reflects analyte levels of a user who is wearing the first analyte sensor, and wherein the first sensor data is collected over a first time period; determine whether data is still being acquired from the first analyte sensor; upon a determination that data is no longer being acquired from the first analyte sensor, classify the first sensor data as intermittent analyte data; and use the intermittent analyte data to generate predicted analyte level data for the user during a second time period that is subsequent to the first time period, wherein the predicted analyte level data is reflective of the intermittent analyte data.

2. The computer system of clause 1, wherein the intermittent analyte data is compared against a repository of baseline sensor data for other users and a result of said comparison is included in a user profile, or, alternatively, the user is not wearing the first analyte sensor during the second time period.

3. The computer system of clause 1 or 2, wherein the predicted analyte level data is compared against metadata associated with the user, wherein the metadata includes one or more of a past glucose level data for the user, location, food consumed, information obtained from a food delivery application, physical activity, or date and time.

4. The computer system of any one of the preceding clauses, wherein the first time period is at least 10 contiguous days.

5. The computer system of any one of the preceding clauses, wherein the first time period is at least 14 contiguous days.

6. The computer system of any one of the preceding clauses, wherein the instructions are further executable to cause the computer system to: acquire new sensor data from a second analyte sensor, different than the first analyte sensor, wherein the second analyte sensor is detected via an application, and wherein the profile is updated using data obtained from the second analyte sensor.

7. The computer system of any one of the preceding clauses, wherein the predicted analyte level data is compared against trending data of other users.

8. The computer system of any one of the preceding clauses, wherein the instructions are further executable to cause the computer system to: determine a standard population trend for multiple other users; and compare a profile of the user against the standard population trend.

9. The computer system of any one of the preceding clauses, wherein a profile of the user includes information relating to meals the user has consumed.

10. The computer system of any one of the preceding clauses, wherein a profile of the user tracks glucose levels associated with a same meal that has previously been consumed by the user, and wherein the profile includes a trend of glucose levels for that meal.

11. The computer system of any one of the preceding clauses, wherein a profile of the user includes glucose level trends for different meals the user has consumed, and wherein the profile includes information relating to a comparison between the different meals.

12. The computer system of any one of the preceding clauses, wherein a profile of the user includes glucose trend levels for different users who all consumed a same meal.

13. The computer system of any one of the preceding clauses, wherein a profile of the user includes supplemental information that is relied on to generate the predicted analyte level data.

14. The computer system of any one of the preceding clauses, wherein a profile of the user is compared against profiles of other users who are in a same demographic group.

15. The computer system of any one of the preceding clauses, wherein the instructions are further executable to cause the computer system to: use a profile of the user to determine a behavioral trend for the user; and perform one or more of: recommend a behavior change to the user; or prompt for additional sensor data.

16. A method for generating an analyte level profile for a user, the method comprising: acquiring first sensor data from an analyte sensor, wherein the first sensor data reflects analyte levels of a user who is wearing the analyte sensor, and wherein the first sensor data is collected over a first time period; using the first sensor data to generate a profile for the user, wherein the profile tracks the analyte levels of the user throughout the first time period; during a second time period that is subsequent to the first time period, determining that sensor data is no longer being acquired from the analyte sensor, resulting in the first sensor data being discontinuous analyte data; using the discontinuous analyte data to generate predicted analyte level data for the user; and updating the profile by including the predicted analyte level data.

17. The method of clause 16, wherein the method further includes prompting the user to put either the analyte sensor or a new analyte sensor on to acquire new data.

18. The method of clause 16 or 17, wherein the profile includes trend data reflecting how a body of the user is becoming more insulin resistant.

19. The method of any one of clauses 16 to 18, wherein supplemental data is added to the profile, and wherein the supplemental data includes data from a hemoglobin A1C test.

20. The method of any one of clauses 16 to 19, wherein the method further includes receiving user input that supplements the discontinuous analyte data, and wherein the user input provides a context for at least some of the discontinuous analyte data.

21. The method of any one of clauses 16 to 20, wherein the method further includes generating a meal score for a meal the user has consumed.

22. The method of clause 21, wherein the meal score is based on glucose level data collected during a time range after the meal was consumed by the user.

23. The method of clause 21 or 22, wherein the meal score is based on one or more of a meal portion size, a meal type, or a listing of ingredients.

24. The method of clause 21, 22 or 23, wherein the meal score is based on an uploaded photograph of the meal.

25. The method of any one of clauses 21 to 24, wherein the profile includes an estimation as to a health level of the meal based on prior meals of a same type as the meal.

26. The method of any one of clauses 21 to 25, wherein the profile includes an estimation as to a health level of the meal based on how other users having similar profile characteristics as the user responded to the meal.

27. The method of any one of clauses 16 to 26, wherein the method further includes: identifying a different user who shares similar profile characteristics as the user; determining that the different user is or has previously consumed a meal similar to a meal the user is or will consume; and use meal-specific analyte levels of the different user to predict meal-specific analyte levels for the user for said meal.

28. The method of any one of clauses 16 to 27, wherein the profile includes glucose fingerprints for the user for different meals.

29. The method of any one of clauses 16 to 28, wherein a machine learning algorithm, which is trained based on analyte training data, generates the predicted analyte level data.

30. The method of any one of clauses 16 to 29, wherein the method further includes training a machine learning algorithm based on the discontinuous analyte data.

31. A method for generating a health model for a user the method comprising: acquiring first sensor data from an analyte sensor, wherein the first sensor data reflects a physiological response of a user who is wearing the analyte sensor, and wherein the first sensor data is collected over a first time period; using the first sensor data to generate the health model for the user, wherein the health model tracks the physiological response of the user throughout the first time period; during a second time period that is subsequent to the first time period, determining that updated sensor data is no longer being acquired from the analyte sensor, resulting in the first sensor data being periodic sensor data; using the periodic sensor data to generate predicted physiological response data for the user during the second time period; and updating the model by including the predicted physiological response data.

32. The method of clause 31, wherein the method further includes: facilitating peer to peer sharing of sensor data; and identifying users who share physiological response characteristics that are similar to the user.

33. The method of clause 31 or 32, wherein the method further includes: accessing one of a calendar or a global positioning system (GPS) data to acquire supplemental data about the user; and associating supplemental data with periodic sensor data using time information, wherein the supplemental data provides context for at least a portion of the periodic sensor data.

34. The method of clause 31, 32 or 33, wherein the method further includes providing a coaching prompt to the user during the second time period.

35. The method of any one of clauses 31 to 34, wherein the method further includes: determining that the predicted physiological response data is stale; and submitting a recommendation to the user to facilitate one or more of: acquiring new sensor data or prompting the user to use a different analyte sensor.

36. The method of clause 35, wherein the predicted physiological response data is determined to be stale after a determined time period has elapsed with no new data from the analyte sensor.

37. The method of clause 36, wherein the first time period is one week or greater.

38. The method of clause 36, wherein the first time period is about one month.

39. The method of any one of clauses 31 to 36, wherein the first time period is between about one month and about six months.

40. The method of any one of clauses 31 to 39, wherein the method further includes: receiving supplemental fitness data; and using the supplemental fitness data to update the health model.

41. The method of clause 40, wherein the supplemental fitness data is one of: blood pressure data, step tracker data, or heart rate data.
42. The device of clause 41, wherein the frequency is based on one or more characteristics of the user.
43. The method of any one of clauses 31 to 42, wherein the method is implemented by a service, and wherein the service is a cloud service.
44. The method of any one of clauses 31 to 43, wherein supplemental data is also used to generate the health model, and wherein different weights are applied to the periodic sensor data and the supplemental data.
45. The method of clause 44, wherein the periodic sensor data includes glucose level data, and wherein the glucose level data is provided a highest weight as compared to weights provided to the supplemental data.
46. The method of any one of clauses 31 to 45, wherein population matching is performed to identify one or more other users who share similar characteristics as the user.
47. The method of clause 46, wherein the similar characteristics include one or more of age, sex, location, activity level, or occupation.
48. The method of clause 46 or 47, wherein a confidence level is determined, and wherein the confidence level reflects how closely the user is similar to the one or more other users.
49. The method of clause 46, 47 or 48, wherein the one or more other users are family members or coworkers.
50. The method of any one of clauses 31 to 49, wherein supplemental data is also fed as input to the health model, and wherein the supplemental data is obtained from one or more of a glucose ketone sensor, a glucose ketone alcohol sensor, or a glucose ketone alcohol lactate sensor.
51. The method of any one of clauses 31 to 50, wherein the model is updated using new sensor data obtained during a period of time that is subsequent to the second time period.
52. A computer system that implements a service that generates a glucose level profile for a user, where the glucose level profile is based on intermittent baseline glucose data received from a continuous glucose monitoring (CGM) sensor and where the glucose level profile includes predicted glucose data that is predicted from the intermittent baseline glucose data, said computer system comprising: a processor system; and a storage system comprising instructions that are executable by the processor system to cause the computer system to service to: acquire first sensor data from a first CGM sensor, wherein the first sensor data reflects glucose levels of a user who is wearing the first CGM sensor, and wherein the first sensor data is collected over a first time period; use the first sensor data to generate a profile for the user, wherein the profile tracks the glucose levels of the user throughout the first time period; during a second time period that is subsequent to the first time period, determine that updated sensor data is either (i) no longer being acquired from the first CGM sensor or (ii) below a threshold level of accuracy, resulting in a determination that the first sensor data is to be classified as being intermittent glucose data; in response to said determination, use the intermittent glucose data to generate predicted glucose level data for the user, wherein the predicted glucose level data is reflective of predicted glucose levels for the user during the second time period; update the profile by including the predicted glucose level data; during a third time period that is subsequent to the second time period, acquire second sensor data from a second CGM sensor worn by the user; and update the profile by including the second sensor data.
53. The computer system of clause 52, wherein the profile is updated via a machine learning engine.
54. The computer system of clause 52 or 53, wherein the service is implemented either on a local client device or in a cloud environment.
55. The computer system of clause 52, 53 or 54, wherein the second CGM sensor is different than the first CGM sensor.
56. The computer system of any one of clauses 52 to 55, wherein the second CGM sensor is the same as the first CGM sensor.
57. The computer system of any one of clauses 52 to 56, wherein a machine learning engine analyzes the second sensor data.
58. The computer system of any one of clauses 52 to 57, wherein a machine learning engine includes analytics on the first sensor data, the predicted glucose level data, and/or the second sensor data in the profile.
59. The computer system of any one of clauses 52 to 58, wherein a machine learning engine, which updates the profile, is included as a part of the service.
60. The computer system of any one of clauses 52 to 59, wherein the service and a machine learning engine, which updates the profile, are included in a same computing architecture.

What is claimed is:

1. A computer system that predicts analyte levels, the computer system comprising:
a processor system; and
a storage system comprising instructions that are executable by the processor system to cause the computer system to:
acquire first sensor data from a first analyte sensor, wherein the first sensor data reflects analyte levels of a user who is wearing the first analyte sensor, and wherein the first sensor data is collected over a first time period;
determine whether data is still being acquired from the first analyte sensor;
upon a determination that data is no longer being acquired from the first analyte sensor, classify the first sensor data as intermittent analyte data;
use the intermittent analyte data to generate predicted analyte level data for the user during a second time period that is subsequent to the first time period, wherein the predicted analyte level data is reflective of the intermittent analyte data;
determine that the predicted analyte level data is stale, wherein determining that the predicted analyte level data is stale comprises designating the predicted analyte level data as unreliable for continued use without acquisition of new sensor data, and wherein determining that the predicted analyte level data is stale comprises:
(i) determining that a time elapsed since acquisition of most recent sensor data from the analyte sensor exceeds a predetermined staleness threshold; or
(ii) determining that a confidence level or accuracy metric associated with the predicted analyte level data has fallen below a threshold value due to an absence of updated sensor data;
in response to determining that the predicted analyte level data is stale, generate a prompt to the user to facilitate acquisition of new analyte sensor data, wherein the prompt instructs the user to use a new analyte sensor to acquire the new analyte sensor data or to facilitate acquiring the new analyte sensor data from the first analyte sensor; and acquire the new analyte sensor data from either the first analyte sensor or the new analyte sensor, wherein the second sensor data is acquired after the prompt is provided to the user.

2. The computer system of claim 1, wherein the intermittent analyte data is compared against a repository of baseline sensor data for other users and a result of said comparison is included in a user profile, or, alternatively, wherein the instructions further cause the computer system to determine if the user is not wearing the first analyte sensor during the second time period.

3. The computer system of claim 1, wherein the predicted analyte level data is compared against metadata associated with the user, wherein the metadata includes one or more of a past glucose level data for the user, location, food consumed, information obtained from a food delivery application, physical activity, or date and time.

4. The computer system of claim 1, wherein the first time period is at least 10 contiguous days.

5. The computer system of claim 1, wherein the first time period is at least 14 contiguous days.

6. The computer system of claim 1, wherein the instructions are further executable to cause the computer system to:

acquire new sensor data from a second analyte sensor, different than the first analyte sensor, wherein the second analyte sensor is detected via an application, and wherein a profile is updated using data obtained from the second analyte sensor.

7. The computer system of claim 1, wherein the predicted analyte level data is compared against trending data of other users.

8. The computer system of claim 1, wherein the instructions are further executable to cause the computer system to:

determine a standard population trend for multiple other users; and compare a profile of the user against the standard population trend.

9. The computer system of claim 1, wherein a profile of the user includes information relating to meals the user has consumed.

10. A method for generating an analyte level profile for a user, the method comprising:

acquiring first sensor data from an analyte sensor, wherein the first sensor data reflects analyte levels of a user who is wearing the analyte sensor, and wherein the first sensor data is collected over a first time period;

using the first sensor data to generate a profile for the user, wherein the profile tracks the analyte levels of the user throughout the first time period;

during a second time period that is subsequent to the first time period, determining that sensor data is no longer being acquired from the analyte sensor, resulting in the first sensor data being discontinuous analyte data;

using the discontinuous analyte data to generate predicted analyte level data for the user;

updating the profile by including the predicted analyte level data;

determining that the predicted analyte level data is stale, wherein determining that the predicted analyte level data is stale comprises designating the predicted analyte level data as unreliable for continued use without acquisition of new sensor data, and wherein determining that the predicted analyte level data is stale comprises:

(i) determining that a time elapsed since acquisition of most recent sensor data from the analyte sensor exceeds a predetermined staleness threshold; or (ii) determining that a confidence level or accuracy metric associated with the predicted analyte level data has fallen below a threshold value due to an absence of updated sensor data;

in response to determining that the predicted analyte level data is stale, generating a prompt to the user to facilitate acquisition of new analyte sensor data, wherein the prompt instructs the user to use a new analyte sensor to acquire the new analyte sensor data or to facilitate acquiring the new analyte sensor data from the first analyte sensor; and acquiring the new analyte sensor data from either the first analyte sensor or the new analyte sensor, wherein the second sensor data is acquired after the prompt is provided to the user.

11. The method of claim 10, wherein the profile includes trend data reflecting how a body of the user is becoming more insulin resistant.

12. The method of claim 10, wherein supplemental data is added to the profile, and wherein the supplemental data includes data from a hemoglobin A1C test.

13. The method of claim 10, wherein the method further includes receiving user input that supplements the discontinuous analyte data, and wherein the user input provides a context for at least some of the discontinuous analyte data.

14. The method of claim 10, wherein the method further includes generating a meal score for a meal the user has consumed.

15. A method for generating a health model for a user the method comprising:

acquiring first sensor data from an analyte sensor, wherein the first sensor data reflects a physiological response of a user who is wearing the analyte sensor, and wherein the first sensor data is collected over a first time period;

using the first sensor data to generate the health model for the user, wherein the health model tracks the physiological response of the user throughout the first time period;

during a second time period that is subsequent to the first time period, determining that updated sensor data is no longer being acquired from the analyte sensor, resulting in the first sensor data being periodic sensor data;

using the periodic sensor data to generate predicted physiological response data for the user during the second time period;

updating the model by including the predicted physiological response data;

determining that the predicted analyte level data is stale, wherein determining that the predicted analyte level data is stale comprises designating the predicted analyte level data as unreliable for continued use without acquisition of new sensor data, and wherein determining that the predicted analyte level data is stale comprises:

(i) determining that a time elapsed since acquisition of most recent sensor data from the analyte sensor exceeds a predetermined staleness threshold; or (ii) determining that a confidence level or accuracy metric associated with the predicted analyte level data has fallen below a threshold value due to an absence of updated sensor data;

in response to determining that the predicted analyte level data is stale, generating a prompt to the user to facilitate acquisition of new analyte sensor data, wherein the prompt instructs the user to use a new analyte sensor to acquire the new analyte sensor data or to facilitate acquiring the new analyte sensor data from the first analyte sensor; and acquiring the new analyte sensor data from either the first analyte sensor or the new analyte sensor, wherein the second sensor data is acquired after the prompt is provided to the user.

16. The method of claim 15, wherein the method further includes:

facilitating peer to peer sharing of sensor data; and identifying users who share physiological response characteristics that are similar to the user.

17. The method of claim 15, wherein the method further includes:

accessing one of a calendar or a global positioning system (GPS) data to acquire supplemental data about the user; and associating supplemental data with periodic sensor data using time information, wherein the supplemental data provides context for at least a portion of the periodic sensor data.

18. The method of claim 15, wherein the method further includes providing a coaching prompt to the user during the second time period.

19. The method of claim 15, wherein the first time period is at least 10 contiguous days.

20. The method of claim 15, wherein the first time period is at least 14 contiguous days.

* * * * *